(12) United States Patent
Matsushima et al.

(10) Patent No.: US 11,261,450 B2
(45) Date of Patent: Mar. 1, 2022

(54) RECOMBINANT CELL, METHOD FOR PRODUCING RECOMBINANT CELL, AND METHOD FOR PRODUCING ISOPRENE OR TERPENE

(71) Applicant: SEKISUI CHEMICAL CO., LTD., Osaka (JP)

(72) Inventors: Kana Matsushima, Tsukuba (JP); Masahiro Furutani, Tsukuba (JP); Kazufumi Kawabata, Tsukuba (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 0 days.

(21) Appl. No.: 16/482,846

(22) PCT Filed: Feb. 14, 2018

(86) PCT No.: PCT/JP2018/004992
§ 371 (c)(1),
(2) Date: Aug. 1, 2019

(87) PCT Pub. No.: WO2018/155272
PCT Pub. Date: Aug. 30, 2018

(65) Prior Publication Data
US 2019/0352647 A1   Nov. 21, 2019

(30) Foreign Application Priority Data
Feb. 27, 2017 (JP) ............................. JP2017-034566

(51) Int. Cl.
*C12N 1/20* (2006.01)
*C12N 15/52* (2006.01)
*C12P 5/02* (2006.01)

(52) U.S. Cl.
CPC ............... *C12N 15/52* (2013.01); *C12P 5/02* (2013.01); *C12Y 503/03002* (2013.01)

(58) Field of Classification Search
CPC .. C12P 5/007; C12P 23/00; C12P 5/00; C12N 1/20; C12Y 402/03027
See application file for complete search history.

(56) References Cited

U.S. PATENT DOCUMENTS

2003/0148479 A1* 8/2003 Keasling ................ C12N 15/52
435/131
2003/0170662 A1   9/2003 Seto et al.
2009/0203102 A1   8/2009 Cervin et al.
2010/0003716 A1   1/2010 Cervin et al.
2010/0086978 A1*  4/2010 Beck ....................... C12P 5/007
435/131
2013/0052692 A1   2/2013 Kirby et al.
2015/0284742 A1  10/2015 Furutani et al.
2015/0337338 A1  11/2015 Furutani et al.
2016/0002672 A1   1/2016 Beck et al.

FOREIGN PATENT DOCUMENTS

| JP | 2009-538601 | 11/2009 |
|----|-------------|---------|
| JP | 2011-505841 | 3/2011 |
| JP | 2011-518564 | 6/2011 |
| JP | 2016-59314 | 4/2016 |
| JP | 2016-511630 | 4/2016 |
| KR | 10-2006-0040494 | 5/2006 |
| WO | 01/64943 | 9/2001 |
| WO | 2007/140339 | 12/2007 |
| WO | 2013/071074 | 5/2013 |
| WO | 2014/065271 | 5/2014 |
| WO | 2014/104202 | 7/2014 |

OTHER PUBLICATIONS

International Preliminary Report on Patentability dated Aug. 27, 2019 in International Application No. PCT/JP2018/004992.
International Search Report dated May 1, 2018 in International Application No. PCT/JP2018/004992.
Supplementary European Search Report dated Nov. 17, 2020 in corresponding European patent application No. 18 75 7230.

* cited by examiner

*Primary Examiner* — Tekchand Saidha
(74) *Attorney, Agent, or Firm* — Wenderoth, Lind & Ponack, L.L.P.

(57) ABSTRACT

Provided is a recombinant cell that produces isoprene or terpene, wherein the recombinant cell includes an ability to synthesize isopentenyl diphosphate through a mevalonate pathway (MVA pathway), wherein the recombinant cell lacks an ability to synthesize isopentenyl diphosphate through an endogenous non-mevalonate pathway (MEP pathway), wherein the recombinant cell includes an isoprene synthase gene or a terpene synthase gene as a foreign gene, and wherein the recombinant cell produces, with the expression of the foreign gene, isoprene or terpene having 10, 15, 20, 30, or 40 carbon atoms. The mevalonate pathway is preferably an exogenous mevalonate pathway.

16 Claims, 2 Drawing Sheets
Specification includes a Sequence Listing.

RECOMBINANT CELL, METHOD FOR PRODUCING RECOMBINANT CELL, AND METHOD FOR PRODUCING ISOPRENE OR TERPENE

TECHNICAL FIELD

The present invention relates to a recombinant cell, a method for manufacturing a recombinant cell, and a method for producing isoprene or terpene. The recombinant cell of the present invention stably maintains an isopentenyl diphosphate synthesis ability through the mevalonate pathway, and has high isoprene or terpene productivity.

BACKGROUND ART

Isoprene is a monomer raw material for synthetic polyisoprene, and is an important material, particularly in the tire industry. On the other hand, terpene is a hydrocarbon having isoprene with five carbon atoms as a constituent unit, and is a group of biological substances that are produced by plants, insects, fungi, and the like. Isoprene and terpenes are used in any fields such as resin materials, perfume raw materials, food additives, detergents, electronic materials, and raw materials for pharmaceuticals and agricultural chemicals, and are indispensable as industrial materials.

Since isoprene is mainly produced through a petrochemical process as a by-product of oil decomposition for naphtha or ethylene production, the sustainability of raw materials vis-a-vis future demands is at risk. Furthermore, since most of the useful terpenes are extracted and purified from natural sources such as plants or essential oils thereof, mass procurement is difficult. Although attempts at chemical synthesis thereof have been made, synthesis of terpene which has a complicated structure requires significant cost and labor. Thus, the existing methods for producing isoprene or terpene have many problems.

In recent years, there has been steady advancement in the development and practical application of techniques for converting to new production processes by means of biotechnology using microorganisms and the like in various substance production fields. Likewise, regarding isoprene or terpene, a production technique with recombinant *Escherichia coli* using sugar as a raw material is known, for example (see Patent Documents 1 and 2, for example). However, all these techniques are just for small-quantity continuous production or transient production with an inducible expression system, and so far, there has been no cases where constant mass-production was achieved. Therefore, particularly in the field of this art, new technique that enables stable mass production has been required. Note here that examples of isoprene production technique with microorganisms (recombinants) other than *E. coli* include the techniques described in Patent Documents 3 and 4, for example.

The production of isoprene or terpene with microorganisms (recombinants) requires synthesizing their precursor isopentenyl diphosphate (IPP) and its isomer, dimethylallyl diphosphate (DMAPP), in large quantities. IPP can be synthesized via two different metabolic pathways, that is, a mevalonate pathway (MVA pathway) and a non-mevalonate pathway (MEP pathway). The mevalonate pathway is present in cytoplasm of a eukaryotic cell, or in some actinomycete or archaeon. The non-mevalonate pathway is present in bacteria and chloroplast of plants and the like.

The mevalonate pathway (MVA pathway) starts with acetyl CoA as a starting substance. Enzymes acting in the mevalonate pathway include, in the order from the upstream, acetyl CoA acetyl transferase, HMG-CoA synthase, HMG-CoA reductase, mevalonate kinase, 5-phosphomevalonate kinase, and diphosphomevalonate decarboxylase.

On the other hand, the non-mevalonate pathway (MEP pathway) starts with glyceraldehyde 3-phosphate and pyruvic acid as starting substances. Enzymes acting in the non-mevalonate pathway include, in the order from the upstream, DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase and HMB-PP reductase.

In the production of isoprene or terpene using bacteria such as *E. coli*, it is considered that introducing an exogenous MVA pathway, which is energetically predominant, in addition to an endogenous MEP pathway can lead to more efficient precursor synthesis. In other words, since the endogenous MEP pathway is under multiple and precise control, it is very difficult to modify it, and there lies a difficultly in modifying the endogenous MEP pathway in an attempt at mass synthesis of IPP as a precursor. Therefore, in order to obtain a large amount of the target product such as isoprene or terpene, it is preferable to improve the precursor synthesis ability using the MVA pathway.

However, when an exogenous MVA pathway is introduced into a host, as the efficiency of precursor synthesis through the MVA pathway is increased, the cytotoxicity caused by an intermediate metabolite in the biosynthetic pathway becomes unignorable. Then, in order to avoid accumulation of such toxicants, mutation occurs in the genes within the MVA pathway, and the host into which the exogenous MVA pathway has been introduced starts actively tolerating genes which have lost their functions. As a result, in a clone into which the exogenous MVA pathway has been introduced and was grown therein, the activity of the MVA pathway is lost, and clones depending on the activity of the endogenous MEP pathway becomes predominant. Such a phenomenon is considered as one of the factors preventing obtainment of stable and highly productive strain of isoprene or terpene. Therefore, in order to improve the production amount of target products such as isoprene or terpene with microorganisms, it is necessary to acquire a clone which does not depend on the MEP pathway and has its IPP synthesis ability through the MVA pathway stabilized, and to improve the precursor synthesis ability through the MVA pathway.

PRIOR ART DOCUMENTS

Patent Documents

Patent Document 1: JP2011-505841 A
Patent Document 2: JP2011-518564 A
Patent Document 3: WO2014/065271
Patent Document 4: WO2014/104202

DISCLOSURE OF INVENTION

Technical Problem

In order to achieve the above-mentioned object, it is desirable, for example, to use a microorganism in which an IPP synthesis ability through the endogenous MEP pathway is deleted and IPP for growth is synthesized only through the MVA pathway. However, a microorganism (recombinant) having such a property (genotype) and producing isoprene or terpene is not known, nor a method for producing isoprene or terpene using such microorganisms is known.

Thus, an object of the present invention is to provide a recombinant cell that enables isoprene or terpene to be mass-produced stably, and a method for producing isoprene or terpene using the recombinant cell.

Solution to Problem

One aspect of the present invention is a recombinant cell that produces isoprene or terpene, wherein the recombinant cell includes a first ability to synthesize isopentenyl diphosphate through a mevalonate pathway, wherein the recombinant cell lacks a second ability to synthesize isopentenyl diphosphate through an endogenous non-mevalonate pathway by deletion of at least one endogenous enzyme selected from the group consisting of DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase, and HMB-PP reductase, wherein the recombinant cell includes, as a first foreign gene, a gene encoding isoprene synthase, a gene encoding monoterpene synthase, a gene encoding sesquiterpene synthase, a gene encoding diterpene synthase, a gene encoding squalene synthase, or a gene encoding phytoene synthase, and wherein the recombinant cell produces, with the expression of the first foreign gene, isoprene or terpene having 10, 15, 20, 30, or 40 carbon atoms.

Preferably, the mevalonate pathway is an exogenous mevalonate pathway.

Preferably, the first ability is achieved by a second foreign gene encoding at least one enzyme selected from the group consisting of acetyl-CoA acetyl transferase, HMG-CoA synthase, HMG-CoA reductase, mevalonate kinase, 5-phosphomevalonate kinase, and diphosphomevalonate decarboxylase.

Preferably, the recombinant cell is a bacterium.

Preferably, the recombinant cell is an archaeon.

Preferably, the recombinant cell can proliferate using at least one selected from the group consisting of carbon monoxide and carbon dioxide as a sole carbon source.

Preferably, the recombinant cell has a function of synthesizing acetyl-CoA from methyl tetrahydrofolate or methyl tetrahydropterin, carbon monoxide, and CoA.

Preferably, the recombinant cell is a *Clostridium* bacterium or a *Moorella* bacterium.

Preferably, the recombinant cell is an archaeon belonging to genus *Methanosarcina*, genus *Methanococcus*, or genus *Methanothermococcus*.

Preferably, the recombinant cell can produce isoprene or terpene from at least one C1 compound selected from the group consisting of methane, methanol, methyl amine, formic acid, formaldehyde, and formamide.

Preferably, the recombinant cell includes, as a formaldehyde fixation pathway, at least one C1 carbon assimilation pathway selected from the group consisting of serine pathway, ribulose monophosphate pathway, and xylulose monophosphate pathway.

Preferably, the recombinant cell belongs to genus *Methylacidphilum*, genus *Methylosinus*, genus *Methylocystis*, genus *Methylobacterium*, genus *Methylocella*, genus *Methylococcus*, genus *Methylomonas*, genus *Methylobacter*, genus *Methylobacillus*, genus *Methylophilus*, genus *Methylotenera*, genus *Methylovorus*, genus *Methylomicrobium*, genus *Methylophaga*, genus *Methylophilaceae*, or genus *Methyloversatilis*.

Preferably, the recombinant cell belongs to genus *Methanosphaera*, genus *Methanosarcina*, genus *Methanolobus*, genus *Methanococcoides*, genus *Methanohalophilus*, and genus *Methanohalobium*.

Another aspect of the present invention is a method for manufacturing the above-described recombinant cell, the method includes: providing a host cell having the second ability to synthesize an isopentenyl diphosphate through a non-mevalonate pathway; deleting the second ability from the host cell; and introducing, as a first foreign gene, a gene encoding isoprene synthase, a gene encoding monoterpene synthase, a gene encoding sesquiterpene synthase, a gene encoding diterpene synthase, a gene encoding squalene synthase, or a gene encoding phytoene synthase into the host cell.

Preferably, the method further includes introducing, as a second foreign gene, a gene encoding at least one enzyme selected from the group, which is an enzyme group acting in a mevalonate pathway, consisting of acetyl-CoA acetyl transferase, HMG-CoA synthase, HMG-CoA reductase, mevalonate kinase, 5-phosphomevalonate kinase, and diphosphomevalonate decarboxylase into the host cell, thereby giving the first ability to synthesize isopentenyl diphosphate through the mevalonate pathway to the host cell.

Another aspect of the present invention is a method for producing isoprene or terpene, the method including: a) bringing at least one C1 compound selected from the group consisting of carbon monoxide, carbon dioxide, formic acid, methane, methanol, methyl amine, formaldehyde, and formamide into contact with the above-described recombinant cell or a recombinant cell manufactured by the above-described method, thereby allowing the recombinant cell to produce isoprene or terpene having 10, 15, 20, 30, or 40 carbon atoms from the C1 compound.

Preferably, the step a) includes: culturing the recombinant cell using at least one C1 compound selected from the group consisting of carbon monoxide, carbon dioxide, formic acid, methane, methanol, methyl amine, formaldehyde, and formamide as a carbon source; and obtaining isoprene or terpene having 10, 15, 20, 30, or 40 carbon atoms from the cultured product.

Effect of Invention

The present invention enables stable production of isoprene or terpene using a recombinant cell.

BEST MODE FOR CARRYING OUT THE INVENTION

Figure 1:
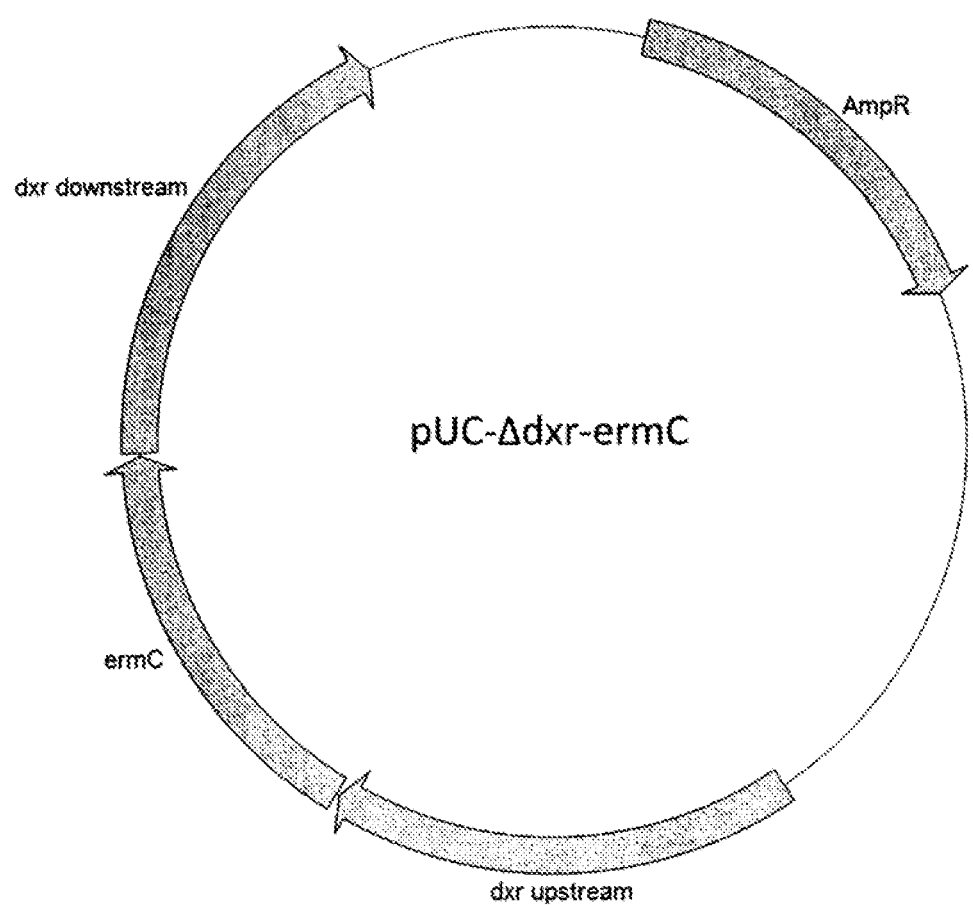
FIG. 1 is an explanatory diagram showing a configuration of plasmid pUC-Δdxr-ermC.

Hereinafter, the exemplary embodiment of the present invention will be described. Note here that in the present invention, all the terms "gene" can be replaced with terms "nucleic acid" or "DNA".

A recombinant cell of the present invention is a recombinant cell that produces isoprene or terpene, wherein the recombinant cell comprises a first ability to synthesize isopentenyl diphosphate through a mevalonate pathway (MVA pathway), and wherein the recombinant cell lacks a second ability to synthesize isopentenyl diphosphate through an endogenous non-mevalonate pathway (MEP pathway). Furthermore, the recombinant cell of the present invention includes, as a foreign gene (first foreign gene), a gene encoding isoprene synthase, a gene encoding monoterpene synthase, a gene encoding sesquiterpene synthase, a gene encoding diterpene synthase, a gene encoding squalene synthase, or a gene encoding phytoene synthase.

<Mevalonate Pathway>

As already described, the mevalonate pathway (MVA pathway) is an isopentenyl diphosphate (IPP) biosynthesis pathway which starts with acetyl CoA as a starting substance. Enzymes acting in the mevalonate pathway include, in the order from the upstream, acetyl CoA acetyl transferase, HMG-CoA synthase, HMG-CoA reductase, mevalonate kinase, 5-phosphomevalonate kinase, and diphosphomevalonate decarboxylase.

The recombinant cell of the present invention has an ability to synthesize isopentenyl diphosphate (isopentenyl diphosphate synthesis ability) through an MVA pathway.

The MVA pathway of the recombinant cell of the present invention includes both an endogenous pathway which the host cell originally has, and an exogenous pathway introduced into the host cell from the outside. When the host cell originally includes a non-mevalonate pathway (MEP pathway) only as an IPP synthesis pathway (prokaryotes such as a bacterium, for example), the MVA pathway is an exogenous pathway. On the other hand, when the host cell originally includes both an MEP pathway and an MVA pathway as an IPP synthesis pathway, the MVA pathway may be an endogenous pathway, an exogenous pathway, or both.

When the exogenous MVA pathway is introduced into the host cell, a gene encoding an enzyme acting in the mevalonate pathway, such as a gene (second foreign gene) encoding an enzyme selected from the group consisting of acetyl-CoA acetyl transferase, HMG-CoA synthase, HMG-CoA reductase, mevalonate kinase, 5-phosphomevalonate kinase, and diphosphomevalonate decarboxylase, can be introduced into a host to be expressed. The enzyme gene to be introduced may be one or a plurality of enzyme genes among the above-mentioned enzyme genes, as long as it has the IPP synthesis ability through the MVA pathway.

The origin of the exogenous MVA pathway, such as the origin of the enzyme group mentioned above (acetyl-CoA acetyl transferase, HMG-CoA synthase, HMG-CoA reductase, mevalonate kinase, 5-phosphomevalonate kinase, diphosphomevalonate decarboxylase), include being derived from eukaryote. Note here that all eukaryotes have an MVA pathway.

However, the MVA pathway is also found in organisms other than eukaryotes. Examples of those having an MVA pathway other than eukaryotes include *Streptomyces* sp. Strain CL190 (Takagi M. et al., J. Bacteriol. 2000, 182 (15), 4153-7), and *Streptomyces griseolosporeus* MF730-N6 (Hamano Y. et al., Biosci. Biotechnol. Biochem. 2001, 65(7), 1627-35) which are actinomycetes.

In bacteria, *Lactobacillus helvecticus* (Smeds A et al., DNA seq. 2001, 12(3), 187-190), *Lactobacillus johnsonii* NCC 533, *Corynebacterium amycolatum, Mycobacterium marinum, Bacillus coagulans, Enterococcus faecalis, Streptococcus agalactiae*, and *Myxococcus xanthus* (Lombard J. et al., Mol. Biol. Evol. 2010, 28(1), 87-99) can be recited.

In archaea, genus *Aeropyrum*, genus *Sulfolobus*, genus *Desulfurococcus*, genus *Thermoproteus*, genus *Halobacterium*, genus *Methanococcus*, genus *Thermococcus*, genus *Pyrococcus*, genus *Methanopyrus*, genus *Thermoplasma* (Lombard J. et al., Mol. Biol. Evol. 2010, 28(1), 87-99) can be recited.

In the present invention, MVA pathways derived from these actinomycetes, bacteria, or archaea can be used as the exogenous MVA pathway.

<Non-Mevalonate Pathway>

A non-mevalonate pathway (MEP pathway) is an isopentenyl diphosphate (IPP) biosynthesis pathway which starts with glyceraldehyde 3-phosphate and pyruvic acid as starting substances. Enzymes acting in the non-mevalonate pathway include, in the order from the upstream, DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase and HMB-PP reductase.

The recombinant cell of the present invention lacks an ability to synthesize isopentenyl diphosphate through an endogenous MEP pathway. Specifically, the activity of at least one endogenous enzyme selected from the group consisting of DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase, and HMB-PP reductase is deleted, and as a result, the IPP synthesis ability through the endogenous MEP pathway is lost.

Examples of the embodiment in which the activity of these enzymes is deleted include an embodiment in which a part or whole of a structural gene encoding an enzyme is deleted, an embodiment in which mutation such as a frame shift is occurring in a structural gene, and the like. Other examples include embodiments in which the expression of the enzyme is not carried out normally due to mutation of a promoter that controls an enzyme gene or mutation in a ribosome binding region. Examples of mutation treatment include irradiation, and treatment with a mutagen such as N-methyl-N'-nitro-N-nitrosoguanidine (NTG) or nitrous acid.

The enzyme in which the activity is deleted may be any one or a plurality of DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase, and HMB-PP reductase.

In a preferable embodiment, at least one or both of DOXP reductoisomerase and HMB-PP synthase is deleted.

<Host Cell>

As the host cell which becomes the basis of the recombinant cell of the present invention, any host cells having an MEP pathway may be employed, and examples thereof include a bacterium. Other candidates include some archaea. Furthermore, from the viewpoint of the carbon source that can be assimilated, the host cell candidates include a so-called syngas assimilating microorganism having an MEP and a methanol assimilating microorganism (methylotroph and the like) having an MEP.

<Syngas Assimilating Microorganism>

Syngas (synthesis gas) is a mixed gas which is efficiently obtained from waste, natural gas, and coal by action of a metal catalyst under high temperature and high pressure, mainly containing carbon monoxide, carbon dioxide, and hydrogen.

In one embodiment of the recombinant cell of the present invention, the recombinant cell may proliferate at least one selected from the group consisting of carbon monoxide and carbon dioxide as a sole carbon source. Furthermore, the recombinant cell preferably has a function of synthesizing acetyl-CoA from methyl tetrahydrofolate or methyl tetrahydropterin, carbon monoxide, and CoA. Having these properties, the recombinant cell of the present invention can produce isoprene or terpene by, for example, assimilating syngas. Examples of such cells (microorganisms) include anaerobic microorganisms having a reduced acetyl-CoA pathway (Wood-Ljungdahl pathway) and a methanol pathway.

Representative examples of such anaerobic microorganisms include *Clostridium* bacteria such as *Clostridium ljungdahlii*, *Clostridium autoethanogenum*, *Clostridium carboxidivorans*, *Clostridium ragsdalei* (Kopke M. et al., Appl. Environ. Microbiol. 2011, 77(15), 5467-5475), *Moorella thermoacetica* (the same as *Clostridium thermoaceticum*) (Pierce E G. Et al., Environ. Microbiol. 2008, 10, 2550-2573) or a *Moorella* bacteria. In particular, *Clostridium* bacteria are preferable as the host cell since their host-vector systems and culture methods have been established.

Examples of the anaerobic microorganism other than the *Clostridium* bacteria and the *Moorella* bacteria include bacteria such as *Carboxydocella sporoducens* sp. Nov. (Slepova T V. et al., Inter. J. Sys. Evol. Microbiol. 2006, 56, 797-800), *Rhodopseudomonas gelatinosa* (Uffen R L, J. Bacteriol. 1983, 155(3), 956-965), *Eubacterium limosum* (Roh H. et al., J. Bacteriol. 2011, 193(1), 307-308), *Butyribacterium methylotrophicum* (Lynd, L H. et al., J. Bacteriol. 1983, 153(3), 1415-1423), and *Oligotropha carboxidovorans*, *Bradyrhizobium japonicum*.

Furthermore, although bacteria have the reduced acetyl-CoA pathway, archaea also have similar pathways. A methyl group donor as a substrate of the acetyl-CoA synthase is methyl tetrahydrofolate and the like in bacteria, but methyl tetrahydropterin and the like in archaea (Diender M. et al., Frontiers in Microbiology 2015, vol. 6, article 1275).

Examples of the anaerobic microorganisms belonging to archaea include genus *Thermococcus*, genus *Methanosarcina*, genus *Methanococcus*, genus *Methanomethylovorans*, genus *Methanothrix*, genus *Methanothermobacter*, genus *Methanomethylophilus*, and genus *Methanosphaera* (Diender M. et al., Frontiers in Microbiology 2015, vol. 6, article 1275; Borrel G. et al., Genome Biol. Evol. 2013, 5(10), 1769-1779). In the present invention, archaea belonging to genus *Methanosarcina*, genus *Methanococcus*, or genus *Methanothermococcus*, can be used, for example.

<Methylotroph>

Methylotroph is a general name for a C1 compound assimilating microorganism that uses a carbon compound not having a C—C bond in the molecule, e.g., methane, methanol, methylamine, dimethylamine, trimethylamine or the like as a sole carbon source or energy source. Any microorganisms called methanotroph, methane-oxidizing bacteria, methanol assimilating bacteria, methanol assimilating yeast, or methanol assimilating microorganism belong to methylotrophs.

Central metabolism of methylotroph is a reaction of converting formaldehyde into an organic matter having a C—C bond after converting methanol to formaldehyde. As a carbon assimilation metabolism pathway via formaldehyde, serine pathway, ribulose monophosphate pathway (RuMP pathway), and xylulose monophosphate pathway (XuMP pathway) can be recited. Methylotrophs classified into bacteria (methylotrophic bacteria) have serine pathway or RuMP pathway. On the other hand, methylotrophs classified into yeast (methylotrophic yeast) has XuMP pathway.

According to the difference in methanol requirement, methylotrophic bacteria are classified into obligate methylotrophs and facultative methylotrophs. The facultative methylotrophs can use other carbon compound.

The recombinant cell of the present invention may be a methylotroph. For example, in one embodiment of the recombinant cell of the present invention, isoprene or terpene can be produced from at least one C1 compound selected from the group consisting of methane, methanol, methyl amine, formic acid, formaldehyde, and formamide. Furthermore, examples of the formaldehyde fixation pathway include at least one C1 carbon assimilation pathway selected from the group consisting of serine pathway, ribulose monophosphate pathway, and xylulose monophosphate pathway.

Examples of methylotroph which can be used in the present invention include methylotrophic bacteria belonging to genus *Methylacidphilum*, genus *Methylosinus*, genus *Methylocystis*, genus *Methylobacterium*, genus *Methylocella*, genus *Methylococcus*, genus *Methylomonas*, genus *Methylobacter*, genus *Methylobacillus*, genus *Methylophilus*, genus *Methylotenera*, genus *Methylovorus*, genus *Methylomicrobium*, genus *Methylophaga*, genus *Methylophilaceae*, genus *Methyloversatilis*, genus *Mycobacterium*, genus *Arthrobacter*, genus *Bacillus*, genus *Beggiatoa*, genus *Burkholderia*, genus *Granulibacter*, genus *Hyphomicrobium*, genus *Pseudomonas*, genus *Achromobacter*, genus *Paracoccus*, genus *Crenothrix*, genus *Clonothrix*, genus *Rhodobacter*, genus *Rhodocyclaceae*, genus *Silicibacter*, genus *Thiomicrospira*, and genus *Verrucomicrobia*.

Microorganism other than bacteria include methylotrophic yeasts belonging to genus *Pichia*, genus *Candida*, genus *Saccharomyces*, genus *Hansenula*, genus *Torulopsis*, and genus *Kloeckera*. Examples of *Pichia* yeasts include *P. haplophila*, *P. pastoris*, *P. trehalophila*, and *P. lindnerii*. Examples of *Candida* yeasts include *C. parapsilosis*, *C. methanolica*, *C. boidinii*, and *C. alcomigas*. Example of *Saccharomyces* yeast includes *Saccharomyces metha-nonfoams*. Examples of *Hansenula* yeasts include *H. wickerhamii*, *H. capsulata*, *H. glucozyma*, *H. henricii*, *H. minuta*, *H. nonfermentans*, *H. philodendra*, and *H. polymorpha*. Examples of *Torulopsis* yeasts include *T. methanolovescens*, *T. glabrata*, *T. nemodendra*, *T. pinus*, *T. methanofloat*, *T. enokii*, *T. menthanophiles*, *T. methanosorbosa*, and *T. methanodomercqii*.

In a preferable embodiment, the recombinant cell belongs to genus *Methylacidphilum*, genus *Methylosinus*, genus *Methylocysti*, genus *Methylobacterium*, genus *Methylocella*, genus *Methylococcus*, genus *Methylomonas*, genus *Methylobacter*, genus *Methylobacillus*, genus *Methylophilus*, genus *Methylotenera*, genus *Methylovorus*, genus *Methylomicrobium*, genus *Methylophaga*, genus *Methylophilaceae*, or genus *Methyloversatilis*. Particularly preferably, the recombinant cell belongs to genus *Methanosphaera*, genus *Methanosarcina*, genus *Methanolobus*, genus *Methanococcoides*, genus *Methanohalophilus*, and genus *Methanohalobium*.

Note here that, by introducing a carbon assimilation metabolism pathway (serine pathway, RuMP pathway, XuMP pathway, and the like) via formaldehyde into a host cell that is non-methylotroph, the non-methylotroph can be handled in the same manner as methylotroph. Introduction of RuMP pathway can be achieved, for example, by introducing a 3-hexulose-6-phosphate synthase (HPS; EC4.1.2.43, for example) gene and a 6-phospho-3-hexuloisomerase (PHI; EC5.3.1.27, for example) gene. Introduction of serine pathway can be achieved, for example, by introducing a serine hydroxymethyl transferase (EC2.1.2.1, for example) gene. Details of such techniques for converting the non-methylotroph into methylotroph is described in, for example, WO2014/104202 (Patent Document 4).

<First Foreign Gene>

In the present invention, the recombinant cell having an isoprene synthase gene as the foreign gene (first foreign gene) can produce isoprene. Furthermore, the recombinant cell having a monoterpene synthase gene as the foreign gene can produce monoterpene (terpene having 10 carbon atoms). Furthermore, the recombinant cell having a sesquiterpene synthase gene as the foreign gene can produce sesquiterpene (terpene having 15 carbon atoms). Furthermore, the recombinant cell having diterpene synthase gene as the foreign gene can produce diterpene (terpene having 20 carbon atoms). Furthermore, the recombinant cell having a squalene synthase gene as the foreign gene can produce triterpene (terpene having 30 carbon atoms). Furthermore, the recombinant cell having a phytoene synthase gene as the foreign gene can produce tetraterpene (terpene having 40 carbon atoms). Hereinafter, each enzyme and each gene are described sequentially.

<Isoprene Synthase>

Isoprene synthase (IspS) has action of converting dimethylallyl diphosphate (DMAPP) as an isomer of isopentenyl diphosphate (IPP) into isoprene. Note here that the structural conversion between the isopentenyl diphosphate and dimethylallyl diphosphate is catalyzed by isopentenyl diphosphate isomerase (IDI). The isopentenyl diphosphate isomerase is present in all organisms.

The isoprene synthase (IspS) used in the present invention is not particularly limited. For example, isoprene synthase derived from eukaryote such as plant can be used. General examples of the isoprene synthase derived from plants include, but not particularly limited to, isoprene synthase derived from *Populus, Stizolobium deeringianum*, and *Pueraria lobata Ohwi*. Specific examples of the isoprene synthase include Q50L36, Q6EJ97, Q9AR86, Q7XAS7, A0PFK2, A0A0M4UQH9, A0A0M5MSL0 (all of the above is UniProtKB entry).

SEQ ID NO: 1 shows an amino acid sequence of the isoprene synthase derived from *Populus nigra* (GenBank Accession No.: AM410988.1).

The isoprene synthase used in the present invention may be not only a naturally occurring and isolated isoprene synthase but also a modified product thereof. For example, it may be proteins that are partial fragments of the existing isoprene synthase or may be amino acid substitution variants and have activity as isoprene synthase.

For example, the isoprene synthase used in the present invention includes at least the following protein (a-1) to (a-3):

(a-1) a protein consisting of an amino acid sequence of SEQ ID NO: 1,
(a-2) a protein consisting of an amino acid sequence in which 1 to 20 amino acids are deleted, substituted, or added in the amino acid sequence of SEQ ID NO: 1, and having isoprene synthase activity, and
(a-3) a protein consisting of an amino acid sequence having identity of 90% or more with the amino acid sequence of SEQ ID NO: 1, and having isoprene synthase activity.

Note here that the identity of an amino acid sequence in (a-3) is more preferably 92% or more, further more preferably 95% or more, and particularly preferably 98% or more.

The possible embodiment further includes a gene encoding isopentenyl diphosphate isomerase (IDI), in addition to the isoprene synthase gene, as a foreign gene. Introduction of the IDI gene enhances the conversion from IPP to DMAPP, and can enhance the isoprene synthesis ability. The IDI used in the embodiment is not particularly limited, and examples thereof include P61615, Q13907, Q46822, P50740, Q8TT35, P15496, Q10132, and Q9KWG2 (UniProtKB entry).

<Monoterpene Synthase>

Monoterpene is terpene having 10 carbon atoms, consisting of two isoprene units. The monoterpene include acyclic monoterpene and cyclic monoterpene. Examples of the acyclic monoterpene include geraniol, myrcene, citral, linalool, and nerol. Examples of the cyclic monoterpene include limonene, α-phellandrene, β-phellandrene, menthol, thymol, α-pinene, β-pinene, carene, carvone, cineol, and camphor.

The monoterpene synthase is a general name of enzymes that convert geranyl diphosphate (GPP) or neryl diphosphate (NPP) into monoterpene. In a synthesis pathway of monoterpene, GPP or NPP is synthesized from isopentenyl diphosphate (IPP) by the action of the GPP synthase (GPPS) or NPP synthase (NPPS). Subsequently, monoterpene is synthesized from GPP or NPP by the action of the monoterpene synthase.

In the preferable embodiment, the monoterpene synthase is cyclic monoterpene synthase. Further preferably, the cyclic monoterpene synthase is phellandrene synthase, and, specifically, it is α-phellandrene synthase or β-phellandrene synthase.

As the α-phellandrene synthase, any enzymes can be used as long as they have activity to generate α-phellandrene from GPP or NPP as a substrate. Examples of the α-phellandrene synthase include G5CV35 and E5GAG2 (UniProtKB entry), and GN65-37361 (SolCyc GeneID), but not particularly limited thereto.

As the β-phellandrene synthase, any enzymes can be used as long they have activity to generate β-phellandrene from GPP or NPP as a substrate. Examples of the β-phellandrene synthase include Q9M7D1, C1K5M3, Q1XBU4, R9QMW3, R9QMR4, R9QMW7, E9N3U9, C0PTH8, F2XFA5, F2XFA1, F2XFA4, and A0A0B0P314 (UniProtKB entry), but not particularly limited thereto.

The monoterpene synthase used in the present invention may be not only a naturally occurring and isolated monoterpene synthase but also a modified product thereof. For example, the monoterpene synthase may be proteins that are partial fragments or amino acid substitution variants of the existing monoterpene synthase and that have monoterpene synthase activity.

For example, the phellandrene synthase (one example of the monoterpene synthase) used in the present invention includes at least the following protein (b-1) to (b-3):

(b-1) a protein consisting of an amino acid sequence of SEQ ID NO: 2,
(b-2) a protein consisting of an amino acid sequence in which 1 to 20 amino acids are deleted, substituted, or added in the amino acid sequence of SEQ ID NO: 2, and having α-phellandrene synthase activity, and
(b-3) a protein consisting of an amino acid sequence having identity of 90% or more with the amino acid sequence of SEQ ID NO: 2, and having α-phellandrene synthase activity.

Note here that the identity of the amino acid sequence in (b-3) is more preferably 92% or more, further more preferably 95% or more, and particularly preferably 98% or more.

Besides, the phellandrene synthase (one example of the monoterpene synthase) used in the present invention includes at least the following protein (c-1) to (c-3):

(c-1) a protein consisting of an amino acid sequence of SEQ ID NO: 3,
(c-2) a protein consisting of an amino acid sequence in which 1 to 20 amino acids are deleted, substituted, or added in the amino acid sequence of SEQ ID NO: 3, and having β-phellandrene synthase activity, and
(c-3) a protein consisting of an amino acid sequence having identity of 90% or more with the amino acid sequence of SEQ ID NO: 3, and having β-phellandrene synthase activity.

Note here that the identity of the amino acid sequence in (c-3) is more preferably 92% or more, further more preferably 95% or more, and particularly preferably 98% or more.

The possible embodiment further includes a gene encoding isopentenyl diphosphate isomerase (IDI), in addition to the monoterpene synthase gene, as a foreign gene. Introduction of the IDI gene enhances the conversion from IPP to DMAPP, and can enhance the GPP synthesis ability or NPP synthesis ability. As a result, it is possible to enhance the monoterpene synthesis ability.

The preferable embodiment further includes a gene encoding GPP synthase (GPPS) or a gene encoding NPP synthase (NPPS), in addition to the monoterpene synthase gene, as a foreign gene. Introduction of these genes can enhance the synthesis ability of monoterpene from GPP or NPP. Examples of the GPPS include S4S927, S4S8D9, D8LHY4, H6VLF6, H6VLF3, D8RV97, Q6V4K1, Q8LKJ3, Q8LKJ2, Q8LKJ1, Q9FSW8, H6VLF7, V5REB1, and Q58GE8 (UniProtKB entry). Examples of the NPPS include NDPS1 derived from *Solanum lycopersicum* (Schilmiller A L et al., PNAS 2009, 106 (26), 10865-10870).

<Sesquiterpene Synthase>

Sesquiterpene is terpene having 15 carbon atoms, consisting of three isoprene units. The sesquiterpene includes acyclic sesquiterpene, monocyclic sesquiterpene, bicyclic sesquiterpene, and tricyclic sesquiterpene. Examples of the acyclic sesquiterpene include farnesene and farnesol. Examples of the monocyclic sesquiterpene include zingiberene, Humulene, and abscisic acid. Examples of the bicyclic sesquiterpene include Caryophyllene, Eudesman, Eremophilan, Valeran, Cadinan, Cadinene, Guajan, Driman, Cedrol, and Nootkatone. Examples of the tricyclic sesquiterpene include Illudan, Prezizaan, Marasman, Cedran, Thujopsan, and Hirsutan.

The sesquiterpene synthase is a general name of enzymes that convert farnesyl diphosphate (FPP) into sesquiterpene. In a synthesis pathway of sesquiterpene, GPP is synthesized from IPP by the action of GPP synthase. Subsequently, FPP is synthesized from GPP by the action of FPP synthase. Subsequently, sesquiterpene is synthesized from FPP by the action of the sesquiterpene synthase.

In the preferable embodiment, the sesquiterpene synthase is cyclic sesquiterpene synthase. In another preferable embodiment, the sesquiterpene synthase is farnesene synthase.

As the farnesene synthase, any enzymes can be used as long as they have activity to generate farnesene from farnesyl diphosphate (FPP) as a substrate. Examples of the farnesene synthase include Q84LB2, B9RXW0, B2KSJ6, and Q84KL5 (UniProtKB entry) for synthesizing an α-form of farnesene ((3E, 6E)-alpha-farnesene), and Q9FXY7, O48935, Q2NM15, C7E5V9, C7E5V7, Q94JS8, C7E5W0, and C7E5V8 (UniProtKB entry), for synthesizing a β-form of the farnesene ((E)-beta-farnesene), but the examples are not particularly limited thereto.

The sesquiterpene synthase used in the present invention may be not only a naturally occurring and isolated sesquiterpene synthase but also a modified product thereof. For example, the sesquiterpene synthase may be proteins that are partial fragments or amino acid substitution variants of the existing sesquiterpene synthase and that have sesquiterpene synthase activity.

For example, the farnesene synthase (sesquiterpene synthase) used in the present invention includes at least the following protein (d-1) to (d-3):
(d-1) a protein consisting of an amino acid sequence of SEQ ID NO: 4,
(d-2) a protein consisting of an amino acid sequence in which 1 to 20 amino acids are deleted, substituted, or added in the amino acid sequence of SEQ ID NO: 4, and having farnesene synthase activity, and
(d-3) a protein consisting of an amino acid sequence having identity of 90% or more with the amino acid sequence of SEQ ID NO: 4, and having farnesene synthase activity.

Note here that the identity of the amino acid sequence in (d-3) is more preferably 92% or more, further more preferably 95% or more, and particularly preferably 98% or more.

The possible embodiment further includes a gene encoding IDI as a foreign gene, in addition to the sesquiterpene synthase gene. Introduction of the IDI gene can enhance the GPP synthesis ability. As a result, it is possible to enhance the FPP synthesis ability, and enhance the sesquiterpene synthesis ability.

The preferable embodiment further includes a gene encoding GPP synthase (GPPS) and/or a gene encoding FPP synthase (FPPS), in addition to the sesquiterpene synthase gene and the like, as a foreign gene. Introduction of these genes enhances synthesis ability of GPP and/or FPP, and, as a result, can enhance the synthesis ability of sesquiterpene. Examples of the GPPS include those listed above. Examples of the FPPS include P08524, P09152, P49349, P14324, P05369, and O014230 (UniProtKB entry). Any one of GPPS gene and FPPS gene may be introduced, or both of them may be introduced.

<Diterpene Synthase>

Diterpene is terpene having 20 carbon atoms, consisting of four isoprene units. The diterpene include acyclic diterpene, monocyclic diterpene, bicyclic diterpene, and tricyclic diterpene. Examples of the acyclic diterpene include α-tocopherol, retinol, and phytol. Examples of the cyclic diterpene include Abietane, Abietic acid, Neoabietic acid, Levomaric acid, Sapietic acid, Atisane, Beyerane, Gibbane, Gibberellic acid, Kaurane, Steviol, Labdane, Picrasane, Pimarane, Podocarpane, Rosane, Taxane, retinal, retinoic acid, and retinol.

The diterpene synthase is a general name of enzymes that convert geranylgeranyl diphosphate (GGPP) into diterpene. In a synthesis pathway of diterpene, GPP is synthesized from IPP by the action of the GPP synthase. Subsequently, FPP is synthesized from GPP by the action of the FPP synthase. Subsequently, GGPP is synthesized from FPP by the action of the GGPP synthase (GGPPS). Subsequently, diterpene is synthesized from GGPP by the action of the diterpene synthase.

As the diterpene synthase, any enzymes can be used as long as they have activity to generate diterpene from GGPP. Examples the diterpene synthase include Q38710, P9WJ61, G9MAN7, M4HY05, H8ZM70, M1VDX3, A2PZA5, Q675L5, Q0E088, P9WJ60, Q6Z5J6, and M4HYP3 (UniProtKB entry), but not particularly limited thereto.

The diterpene synthase used in the present invention may be not only a naturally occurring and isolated diterpene synthase but also a modified product thereof. For example, the diterpene synthase may be proteins that are partial fragments or amino acid substitution variants of the existing diterpene synthase and that have diterpene synthase activity.

The possible embodiment further includes a gene encoding IDI, in addition to the diterpene synthase gene, as a foreign gene. Introduction of the IDI gene can enhance GPP synthesis ability. As a result, the FPP synthesis ability and GPP synthesis ability are strengthened, and the diterpene synthesis ability can be enhanced.

The preferable embodiment further includes at least one gene selected from the group consisting of a gene encoding GPP synthase (GPPS), a gene encoding FPP synthase (FPPS), and a gene encoding GGPP synthase (GGPPS), in addition to the diterpene synthase gene, as a foreign gene. Introduction of these genes enhances the synthesis ability of GPP, FPP, or GGPP. As a result, the diterpene synthesis ability can be enhanced. Examples of the GPPS or the FPPS include those listed above. Examples of the GGPPS include Q12051, Q84J75, P34802, P80042, Q94ID7, Q9SLG2, Q9C446, Q54BK1, Q9LUE1, Q92236, Q39108, O95749, Q12051, Q9P885, and P24322 (UniProtKB entry).

Any one of the GPPS gene, the FPPS gene, and the GGPPS gene may be introduced, or two or more thereof may be introduced.

The preferable embodiment further includes a gene encoding copalyl diphosphate synthase (CPPS), in addition to the diterpene synthase gene, as a foreign gene. Copalyl diphosphate (CPP) is a GGPP derivative having 20 carbon atoms. When the CPP synthase gene is introduced, a substrate of the diterpene synthase may be CPP. Examples of the CPPS include G8HZG6, O22667, A0A0N7I618, and Q0Q2G7 (UniProtKB entry).

<Squalene Synthase>

Triterpene is terpene having 30 carbon atoms, consisting of six isoprene units. In general, squalene (C30) as acyclic triterpene is generated by dimerization of FPP (C15) (through catalysis of squalene synthase), 2,3-Oxidosqualene (2,3-epoxy-2,3-dihydroaqualene) is generated from squalene, and 200 types or more of triterpene skeletons can be biosynthesized through cyclization of 2,3-Oxidosqualene. However, since the generation of 2,3-Oxidosqualene from squalene has an oxygen requirement property, triterpene that can be produced by the recombinant cell that is an anaerobic archaeon of the present invention is mainly Hopene, Hopanol, and Hopanoid compounds as the derivative thereof, which are generated by the cyclization of squalene.

As described above, squalene synthase (SS) (EC 2.5.1.21) has action of dimerizing FPP. When the Hopanoid compound is synthesized, at least Squalene/Hopene cyclase (EC 5.4.99.17) gene, or Squalene/Hopanol cyclase (EC 4.2.1.129) gene, in addition to squalene synthase gene, may be introduced. In general, the Squalene/Hopene cyclase also has Squalene/Hopanol cyclization enzymatic activity. Examples of the squalene synthase (SS) include P53799, P36596, P29704, P37268, P52020, Q9HGZ6, Q9Y753, Q9SDW9, and P78589 (UniProtKB entry). Examples of the Squalene/Hopene (Squalene/Hopanol) cyclase include P33247, P33990, P54924, and P55348 (UniProtKB entry).

Further introduction of the IDI gene in addition to the SS gene can enhance the squalene synthesis ability. Furthermore, in addition, introduction of the geranyl diphosphate synthase (GPPS) gene and/or the farnesyl diphosphate synthase (FPPS) gene can enhance the synthesis ability of squalene. Examples of the GPPS and FPPS are those listed above.

The squalene synthase used in the present invention may be not only a naturally occurring and isolated squalene synthase but also a modified product thereof. For example, the squalene synthase may be proteins that are partial fragments or amino acid substitution variants of the existing squalene synthase and that have squalene synthase activity.

<Phytoene Synthase>

Tetraterpene is terpene having 40 carbon atoms, consisting of eight isoprene units, and mainly includes a compound group called carotenoid. Tetraterpene include many acyclic tetraterpenes or cyclic tetraterpenes. The acyclic tetraterpenes include phytoene, lycopene, and neurosporene. The monocyclic tetraterpene includes γ-carotene. The bicyclic tetraterpene includes α-carotene, β-carotene, astaxanthin, antheraxanthin, canthaxanthin, capsanthin, β-cryptoxanthin, lutein, myxoxanthophyll, zeaxanthin, fucoxanthin, rhodoxanthin, neoxanthin, and flavoxanthin.

Phytoene synthase (PYS) (EC 2.5.1.32) has action of dimerizing geranylgeranyl diphosphate (GGPP). Examples of the PYS include Q7Z859, Q9P854, P37272, Q67GH9, D5KXJ0, P21683, Q9UUQ6, P08196, B2ATB0, Q2U4X9, A2QM49, P37271, P37273, P49085, P54975, P9WHP3, P54977, P22872, and P17056 (UniProtKB entry).

Further introduction of the IDI gene in addition to the PSY gene can enhance the phytoene synthesis ability. Furthermore, introduction of at least one gene selected from the group consisting of a GPP synthase gene, an FPP synthase gene, and a GGPP synthase gene can enhance the synthesis ability of phytoene. Examples of the GPPS, FPPS, and GGPPS are those listed above.

The phytoene synthase used in the present invention may be not only a naturally occurring and isolated phytoene synthase but also a modified product thereof. For example, the phytoene synthase may be proteins that are partial fragments or amino acid substitution variants of existing phytoene synthase and that have phytoene synthase activity.

As described above, the recombinant cell of the present invention includes an isoprene synthase gene, a monoterpene synthase gene, a sesquiterpene synthase gene, a diterpene synthase gene, a squalene synthase gene, or a phytoene synthase gene as a foreign gene, and further optionally includes an IDI gene, a GPPS gene, an NPPS gene, a GGPPS gene, a CPPS gene, an SS gene, and the like.

<Method for Manufacturing Recombinant Cell>

The recombinant cell of the present invention can be manufactured using, for example, a host cell having an ability to synthesize an isopentenyl diphosphate through a non-mevalonate pathway, and a gene encoding isoprene synthase or terpene synthase. For example, the recombinant cell of the present invention can be manufactured by the method including the following steps (1) to (3):

(1) a first step of providing a host cell having the ability to synthesize an isopentenyl diphosphate through a non-mevalonate pathway, (2) a second step of deleting the ability to synthesize an isopentenyl diphosphate through a non-mevalonate pathway from the host cell, and (3) a third step of introducing, as a first foreign gene, a gene encoding isoprene synthase, a gene encoding monoterpene synthase, a gene encoding sesquiterpene synthase, a gene encoding diterpene synthase, a gene encoding squalene synthase, or a gene encoding phytoene synthase into the host cell.

In the first step, a host cell having an isopentenyl diphosphate (IPP) synthesis ability through the non-mevalonate pathway (MEP pathway) is provided. For example, a cell that synthesizes IPP through the MEP pathway, such as a bacterium, is prepared as a host cell.

In the second step, the isopentenyl diphosphate (IPP) synthesis ability through the non-mevalonate pathway (MEP pathway) of a host cell is deleted. For example, deleted is an action of at least one enzyme selected from the group consisting of DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase, and HMB-PP reductase, that is, an enzyme group acting in the MEP pathway. Examples of the technique for deleting the enzymatic activity includes deleting a part or whole of the enzyme gene, introducing a mutation (frameshift, etc.) into an enzyme gene, introducing a mutation into a promoter or a ribosome binding region, and the like. Examples of the mutation treatment include irradiation, treatment with a mutagen (NTG, nitrous acid, etc.), and the like. The enzyme whose activity is deleted may be one enzyme or a plurality of enzymes.

In a preferable embodiment, the activity of at least one or both of DOXP reductoisomerase and HMB-PP synthase is deleted.

In the third step, a gene encoding isoprene synthase, a gene encoding monoterpene synthase, a gene encoding sesquiterpene synthase, a gene encoding diterpene synthase, a gene encoding squalene synthase, or a gene encoding phytoene synthase is introduced as the first foreign gene into the host cell. This makes it possible to obtain a recombinant cell that produces isoprene or terpene in which the isopentenyl diphosphate synthesis ability through the endogenous MEP pathway is deleted. Note here that the IPP synthesis can be carried out through an endogenous MVA pathway, or through an exogenous MVA pathway to be additionally introduced.

Note here that the order in which the second step and the third step are carried out does not matter in this method. In other words, the first foreign gene may be introduced after the activity of the endogenous MEP pathway is deleted, or alternatively, the activity of the endogenous MEP pathway may be deleted after the first foreign gene is introduced. Both steps may be carried out simultaneously.

A preferable embodiment carries out the following step (4) in addition to the above steps (1) to (3):

(4) a fourth step of introducing, as a second foreign gene, a gene encoding at least one enzyme selected from the group, which is an enzyme group acting in a mevalonate pathway, consisting of acetyl-CoA acetyl transferase, HMG-CoA synthase, HMG-CoA reductase, mevalonate kinase, 5-phosphomevalonate kinase, and diphosphomevalonate decarboxylase into the host cell, thereby giving the ability to synthesize isopentenyl diphosphate through the mevalonate pathway to the host cell. When the host cell does not include an endogenous mevalonate pathway (MVA pathway), the fourth step is basically required. The second foreign gene to be introduced may be any one or a plurality of the enzyme genes as long as the IPP synthesis ability through the MVA pathway can be provided.

Note here that the order in which the second step, the third step and the fourth step are carried out does not matter in this method. However, it is preferable that the fourth step is carried out prior to the second step. In other words, it is preferable that the endogenous MEP pathway is deleted after the second foreign gene is introduced. Furthermore, the third step and the fourth step can be carried out simultaneously. For example, the third and fourth steps can be carried out simultaneously by incorporating a first foreign gene and a second foreign gene into one vector and introducing the vector into a host cell.

<Gene Introduction Method>

The method of introducing a gene into the host cell is not particularly limited, and may be selected appropriately depending on the kind of the host cell and the like. For example, a vector that can be introduced into the host cell and can allow expression of the gene incorporated therein may be used. For example, when the host cell is a prokaryote such as a bacterium, a vector that can self duplicate or can be incorporated in chromosome in the host cell, and contains a promoter at the position allowing transcription of the inserted gene can be used. For example, it is preferred to construct in the host cell a series of structures including a promoter, a ribosome binding sequence, the above gene (DNA) and a transcription termination sequence by using the vector.

A case where the host cell is a *Clostridium* bacterium (including related species such as *Moorella* bacteria) is described. A shuttle vector pIMP1 between *Clostridium* bacterium and *Escherichia coli* (Mermelstein L D et al., Bio/technology 1992, 10, 190-195) may be used. The shuttle vector is a fusion vector of pUC9 (ATCC 37252) and pIM13 isolated from *Bacillus subtilis* (Projan S J et al., J. Bacteriol. 1987, 169 (11), 5131-5139) and is retained stably in the *Clostridium* bacterium.

For gene introduction into the *Clostridium* bacterium, an electroporation method is generally used. However, the introduced exogenous plasmid immediately after gene introduction is liable to be decomposed by a restriction enzyme Cac824I and the like, and is therefore very instable. For this reason, it is preferred to once amplify the vector from pIMP1 in *E. coli*, for example, strain ER2275 having pAN1 (Mermelstein L D et al., Apply. Environ. Microbiol. 1993, 59(4), 1077-1081) carrying a methyl transferase gene from *Bacillus subtilis* phage Φ3T1, followed by a methylation treatment, and to recover the resultant vector from *E. coli* for use in transformation by electroporation. Recently, Cac824I gene-deficient *Clostridium acetobutylicum* has been developed, and make it possible to stably carry a vector which is not subjected to a methylation treatment (Dong H. et al., PLoS ONE 2010, 5 (2), e9038).

Examples of the promoter for heterologous gene expression in *Clostridium bacteria* include thl (thiolase) promoter (Perret S et al., J. Bacteriol. 2004, 186(1), 253-257), Dha (glycerol dehydratase) promoter (Raynaud C. et al., PNAS 2003, 100(9), 5010-5015), ptb (phosphotransbutyrylase) promoter (Desai R P et al., Appl. Environ. Microbiol. 1999, 65(3), 936-945), and adc (acetoacetate decarboxylase) promoter (Lee J et al., Appl. Environ. Microbiol. 2012, 78 (5), 1416-1423). However, in the present invention, sequences of promoter regions used in operons of various metabolic systems found in the host cell or the like may be used without limited to the above examples.

A case where the host cell is the methylotroph bacterium is described. As a method of incorporating into chromosome of a methylotroph bacterium, exemplified is a method of destroying a target gene in *Methylobacillus flagellatus* having a ribulose monophosphate pathway, and in *Methylobacterium extorquencs* having serine pathway (Chistoserdova L. et al., Microbiology 2000, 146, 233-238; Chistoserdov A Y., et al., J. Bacteriol 1994, 176, 4052-4065). While these are the methods for introducing a gene into a genome using cyclic DNA, a method for introducing a gene into genome using a linear DNA is also developed in *Methylophilus* bacteria and the like (see JP 2004-229662 A). In general, genomic recombination is more efficient by linear DNA than by cyclic DNA when the DNA is less susceptible to degradation by the host cell. Generally, in a homologous recombination method, it is preferred to target a gene existing in multi copies on the genome likewise an inverted-repeat sequence. As a technique for introducing multi copies into a genome, a method of carrying on a transposon is also known besides the homologous recombination. As a method of introducing a gene into a methylotrophic bacterium by a plasmid, for example, pAYC32 (Chistoserdov A Y., et al., Plasmid 1986, 16, 161-167), pRP301 (Lane M., et al., Arch. Microbiol. 1986, 144(1), 29-34), pBBR1, pBHR1 (Antoine R. et al., Molecular Microbiology 1992, 6, 1785-1799), and pCM80 (Marx C J. et al., Microbiology 2001, 147, 2065-2075) which are broad host range vectors are known.

A case where the host cell is the archaeon is described. For example, a shuttle vector with *E. coli* based on a plasmid pC2A that is included in *Methanosarcina* can be used (Sowers K. R. et al., J. Bacteriol. 1988, 170, 4979-4982; Metcalf W. W. et al., PNAS 1997, 94, 2626-2631). Examples of introduction and deletion of gene by homologous recombination are disclosed (Rother M., et al., J. Bacteriol 2005, 187, 5552-5559; Conway D. M., J. Mol. Biol. 1996, 262, 12-20). These techniques can be used also in the present invention. As an expression system, inducible or constitutive expression techniques using a regulation system of tetracycline resistance gene expression can be used (Guess A. M. et al., Archaea 2008, 2, 193-203).

In introducing plural kinds of genes by using a vector, the genes may be incorporated into one vector, or incorporated into different vectors. Further, in incorporating a plurality of genes into one vector, the genes may be expressed under a common promotor, or may be expressed under different promotors. As an example of introducing plural kinds of genes, an embodiment of introducing the first foreign gene and the second foreign gene is recited.

By further conducting mutation or genome shuffling in addition to the introduction of exogenous nucleic acid as described above, it is possible to breed a bacterial strain exhibiting dramatically increased productivity of isoprene or terpene.

<Method for Producing Isoprene or Terpene>

The method for producing isoprene or terpene of the present invention includes: bringing at least one C1 compound selected from the group consisting of carbon monoxide, carbon dioxide, formic acid, methane, methanol, methyl amine, formaldehyde, and formamide into contact with the above-described recombinant cell or a recombinant cell manufactured by the above-described method, thereby allowing the recombinant cell to produce isoprene or terpene having 10, 15, 20, 30, or 40 carbon atoms from the C1 compound. Typically, the method includes culturing the recombinant cell using at least one C1 compound selected from the group consisting of carbon monoxide, carbon dioxide, formic acid, methane, methanol, methyl amine, formaldehyde, and formamide as a carbon source; and obtaining isoprene or terpene having 10, 15, 20, 30, or 40 carbon atoms from the cultured product.

The C1 compound used as a carbon source may be used singly or in combination of two or more. Furthermore, the C1 compound is preferably used as a main carbon source, and more preferably as a sole carbon source. Furthermore, it is preferable to concurrently provide hydrogen ($H_2$) as an energy source.

The method for culturing the recombinant cell of the present invention is not particularly limited, and can be appropriately carried out depending on the type of the host cell, and the like. When the recombinant cell is a *Clostridium* bacterium (strictly anaerobic), it is cultured, for example, in a nutrient condition including inorganic salts required for growth, and syngas. Preferably, it is cultured under a pressurized condition at about 0.2 to 0.3 MPa (absolute pressure). Furthermore, for improving initial proliferation and attained cell density, small amounts of organic substances such as vitamins, yeast extract, corn steep liquor, and Bacto Tryptone, may be added.

Note here that the recombinant cell is aerobic or facultative anaerobic, for example, it may be cultured in a liquid medium under aeration and stirring.

The recombinant cell may be provided with a gas mainly containing carbon monoxide and hydrogen, or a gas mainly containing carbon dioxide and hydrogen. In other words, isoprene or terpene is produced from carbon monoxide or carbon dioxide in such a gas by culturing the recombinant cell by using the above-mentioned gas as a carbon source, or by bringing the above-mentioned gas into contact with the recombinant cell. Also in this case, hydrogen is used as an energy source.

Isoprene or terpene may be produced from formic acid and/or methanol by providing the recombinant cell with formic acid and/or methanol. In other words, isoprene or terpene can also be produced from formic acid and/or methanol by culturing the recombinant cell using, as a carbon source, formic acid or methanol solely or in addition to carbon monoxide and/or carbon dioxide, or by bringing formic acid and/or methanol into contact with the recombinant cell.

The production of isoprene or terpene can be carried out without culturing the recombinant cell. That is, isoprene or terpene can be produced by bringing the above-mentioned C1 compound into contact with the recombinant cell regardless of whether or not cell division (cell proliferation) occurs. For example, the above-mentioned C1 compound is continuously fed to the immobilized recombinant cell, so that isoprene or terpene can be continuously produced. Also in this case, the C1 compound as a carbon source may be used singly or in combination of two or more. Furthermore, it is preferable to bring hydrogen ($H_2$) into contact concurrently as an energy source.

The produced isoprene or terpene can be recovered from, for example, the outside of the cells, that is, a cultured broth or a gas phase fraction.

In the following, the present invention will be described more specifically by way of examples. However, the present invention is not limited to these examples.

Example 1

In this Example, the production amount of isoprene was compared between a recombinant cell of *Clostridium ljungdahlii* that is one type of syngas assimilating bacteria, and an MEP pathway-deficient recombinant cell.

(1) Construction of Various Vectors

Referring to Appl Biochem Biotechnol (2012) 168: 1384-1393, pUC-Δdxr-ermC (SEQ ID No: 6) including the upstream sequence of a DOXP reductoisomerase gene dxr of *C. ljungdahlii* (CLJU_c13080), an erythromycin-resistant gene (*Staphylococcus aureus*-derived ermC gene, SEQ ID No: 5, GenBank Accession No.: KX011076), and the downstream sequence of DOXP reductoisomerase gene dxr of *C. ljungdahlii* was prepared. The configuration of pUC-Δdxr-ermC is shown in FIG. 1. In the drawing, "dxr upstream" indicates the upstream sequence of the DOXP reductoisomerase gene, "dxr downstream" indicates the downstream sequence of the DOXP reductoisomerase gene, "ermC" indicates the erythromycin resistant gene, and "AmpR" indicates the ampicillin resistant gene.

pJIR750ai (Sigma-Aldrich) as a *Clostridium/E. coli* binary vector was modified to construct pSK1(LbMVA-ISPS) (SEQ ID No: 10) including a nucleotide sequence in which a *lactobacillus*-derived mevalonate pathway gene cluster (derived from *Lactobacillus johnsonii* NCC 533, SEQ ID No: 7, SEQ ID No: 8, GenBank Accession No.: AE017198.1), an isoprene synthase gene (poplar-derived IspS gene, SEQ ID No: 9, GenBank Accession No.: AM410988.1), and a chloramphenicol resistant gene (derived from pJIR750ai) were codon-modified.

Figure 2:
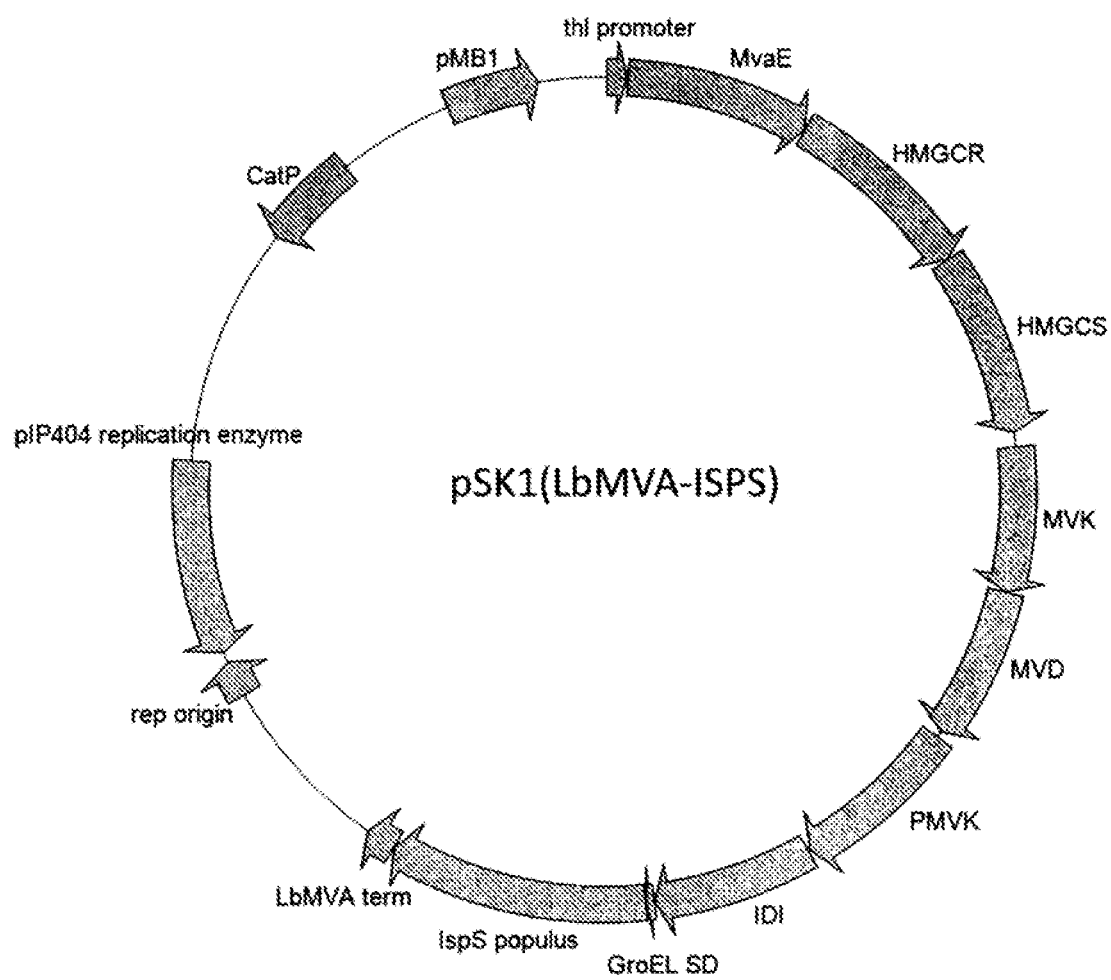
FIG. 2 is an explanatory diagram showing a configuration of plasmid pSK1(LbMVA-ISPS).

The configuration of pSK1(LbMVA-ISPS) is shown in FIG. 2. In the drawing, "MvaE" indicates an acetyl-CoA acetyl transferase gene, "HMGCR" indicates an HMG-CoA reductase gene, "HMGCS" indicates an HMG-CoA synthase gene, "MVK" indicates a mevalonate kinase gene, "MVD" indicates a diphosphomevalonate decarboxylase gene, "PMVK" indicates a phosphomevalonate kinase gene, and "IDI" indicates an isopentenyl diphosphate isomerase gene, respectively. Furthermore, "IspS populous" indicates a sequence of the poplar-derived isoprene synthase (partially codon-modified for *Clostridium*), "GroEL SD" indicates an upper SD sequence of the chaperonin GroEL gene of *C. ljungdahlii*, and "thl promoter" indicates a thiolase promoter of *C. acetobutylicum*. In addition, "pMB1" indicates ori of *E. coli*, "CatP" indicates a chloramphenicol resistant gene, "rep origin" indicates a replication origin of *Clostridium*, and "pIP404 replication enzyme" indicates a replication enzyme in the *Clostridium*.

(2) Gene Introduction into DSM13528/ATCC55383 Strain

By using a technique described in Leang C. et al., Appl Environ Microbiol. 2013 79(4), 1102-9, pSK1(LbMVA-ISPS) was introduced into a DSM13528/ATCC55383 strain by an electroporation method. Screening was carried out using an ATCC1754 agar medium containing 5 µg/mL thiamphenicol (1.5% agar, containing fructose) to obtain an isoprene-producing strain SK1. The SK1 strain had both an endogenous MEP pathway and an exogenous MVA pathway.

(3) Preparation of MEP Pathway-Deficient (dxr Gene Knockout) *Clostridium* Strain By using a technique recommended in Leang C. et al., Appl Environ Microbiol. 2013 79 (4), 1102-9, pUC-Δdxr-Cat was introduced into a SK1 strain. Screening was carried out in an ATCC1754 agar medium (1.5% agar) including 4 µg/mL Clarithromycin and 5 µg/mL thiamphenicol, respectively, and dxr was deleted by homologous recombination. Thus, the isoprene producing strain SK2 which lacked the endogenous MEP pathway and grew while depending on the exogenous MVA pathway was manufactured.

(4) Isoprene Quantification

The SK1 strain and the SK2 strain were cultured at 37° C. in anaerobic condition. Inoculation was carried out in 5 mL of 5 µg/mL thiamphenicol-containing ATCC1754 medium (pH=5.0, fructose not contained). A 27 mL-volume hermetically-sealable headspace vial vessel was charged with a mixed gas of $CO/CO_2/H_2$=33/33/34% (volume ratio). The vial was filled with the mixed gas at a gas pressure of 0.25 MPa (absolute pressure), hermetically sealed with an aluminum cap, followed by shaking culture. For the cultured products in which proliferation was observed, culture was terminated at the time when OD600 reached 1.0, and the vapor phase was analyzed using a gas chromatograph mass spectrometer (GCMS-QP2010 Ultra, manufactured by Shimadzu Corporation).

As a result, both in the SK1 strain and the SK2 strain, isoprene was detected in the production amount of 10 mg isoprene/dried cell (g) on average.

According to the above, the recombinant cell of *C. ljungdahlii*, which lacked its endogenous MEP pathway but had the exogenous MVA pathway functioning, was able to produce isoprene in an amount which was equivalent to that of the recombinant cell having both the endogenous MEP pathway and the exogenous MVA pathway. That is to say, regardless of whether the endogenous MEP pathway was present or not, the exogenous MVA pathway enabled the production of isoprene in an equivalent amount.

Example 2

In this Example, the SK1 strain and the SK2 strain prepared in Example 1 were used, and production stability of isoprene in each strain was examined.

(1) Subculture Experiment of Recombinant Cell

Five clones each for the SK1 strain and the SK2 strain were inoculated in 5 mL of 5 µg/mL thiamphenicol-containing ATCC1754 medium containing (pH=5.0, fructose not contained). A 27 mL-volume hermetically-sealable headspace vial vessel was charged with a mixed gas of $CO/CO_2/H_2$=33/33/34% (volume ratio). The vial was filled with the mixed gas at a gas pressure of 0.25 MPa (absolute pressure), and hermetically sealed with an aluminum cap, followed by shaking culture. At the time when OD600 reached 1.0, each strain was inoculated again in a new ATCC1754 medium (subculture). This subculture step was repeated 20 times. As a result, proliferation was observed in all clones even after the 20th subculture.

(2) Plasmid Stability and Isoprene Productivity

Referring to "Isolation of Plasmid DNA from *Bacillus subtilis* using the QIAprep Spin Miniprep Kit-(EN)", plasmid pSK1(LbMVA-ISPS) was extracted from each clone of the SK1 strain and the SK2 strain using QIAprep Spin Miniprep Kit (QIAGEN). The extracted DNA was transformed into *E. coli* JM109 (Takara Bio Inc.), and a plasmid was extracted again from 10 colonies among the obtained colonies using QIAprep Spin Miniprep Kit. The nucleotide sequence of the obtained plasmid was analyzed using Applied Biosystems 3130 Genetic Analyzer (Applied Biosystems).

As a result, in the plasmid derived from each clone of the SK1 strain, at least one or more mutations were generated in a mevalonate pathway gene cluster sequence, and it was considered that the function of the MVA pathway was lost. Note here that mutation to a drug resistance gene sequence was not observed. On the other hand, in the plasmid derived from each clone of the SK2 strain, no mutation was observed in any of the mevalonate pathway gene cluster sequence nor the drug resistance gene sequence, and the MVA gene cluster was maintained normally even after subculturing for 20 times.

Furthermore, the vapor phase of the vial bottle after the SK1 strain and the SK2 strain were subcultured 20 times was analyzed by gas chromatograph mass spectrometer (GCMS-QP2010 Ultra). As a result, all clones of the strain SK1 produced isoprene in an amount below the detection limit of the gas chromatograph mass spectrometer. On the other hand, in the SK2 strain, isoprene was detected in all clones in the production amount of 10 mg isoprene/dry cell (g) on average.

According to the above, by introducing an exogenous mevalonate pathway for synthesizing a precursor (IPP) of isoprene into a host cell and knocking out an endogenous non-mevalonate pathway gene of a host, a recombinant cell which had only an exogenous mevalonate pathway functioning as a synthesis pathway of IPP was prepared. Also, it was shown that the recombinant cell in which isoprene synthase gene was introduced can stably maintain the function of the exogenous mevalonate pathway, and stably and continuously produce isoprene.

The invention claimed is:

1. A recombinant cell that produces isoprene,
   wherein the recombinant cell is a *Clostridium* bacterium or a *Moorella* bacterium,
   wherein the recombinant cell comprises a first ability to synthesize isopentenyl diphosphate through an exogenous mevalonate pathway,
   wherein the recombinant cell lacks a second ability to synthesize isopentenyl diphosphate through an endogenous non-mevalonate pathway by deletion of at least one endogenous enzyme selected from the group consisting of 1-deoxy-D-xylulose 5-phosphate (DOXP) synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, (E)-4-hydroxy-3-methyl-but-2-enyl pyrophosphate (HMB-PP) synthase, and HMB-PP reductase,
   wherein the recombinant cell comprises a first foreign gene encoding isoprene synthase,
   wherein the recombinant cell comprises a second foreign gene to achieve the first ability, the second foreign gene comprising:
      a gene encoding acetyl-CoA acetyl transferase;
      a gene encoding hydroxymethylglutaryl-CoA (HMG-CoA) synthase;
      a gene encoding HMG-CoA reductase;
      a gene encoding mevalonate kinase;
      a gene encoding 5-phosphomevalonate kinase; and
      a gene encoding diphosphomevalonate decarboxylase,
   wherein the recombinant cell produces isoprene with the expression of the first foreign gene, and
   wherein the recombinant cell stably and continuously comprises the first ability even after repeated subculture.

2. The recombinant cell according to claim 1, wherein the recombinant cell is an archaeon.

3. The recombinant cell according to claim 1, wherein the recombinant cell can proliferate using at least one selected from the group consisting of carbon monoxide and carbon dioxide as a sole carbon source.

4. The recombinant cell according to claim 1, wherein the recombinant cell has a function of synthesizing acetyl-CoA from methyl tetrahydrofolate or methyl tetrahydropterin, carbon monoxide, and CoA.

5. The recombinant cell according to claim 3, wherein the recombinant cell is an archaeon belonging to genus *Methanosarcina*, genus *Methanococcus*, or genus *Methanothermococcus*.

6. The recombinant cell according to claim 1, wherein the recombinant cell can produce isoprene or terpene from at least one C1 compound selected from the group consisting of methane, methanol, methyl amine, formic acid, formaldehyde, and formamide.

7. The recombinant cell according to claim 6, wherein the recombinant cell comprises, as a formaldehyde fixation pathway, at least one C1 carbon assimilation pathway selected from the group consisting of serine pathway, ribulose monophosphate pathway, and xylulose monophosphate pathway.

8. The recombinant cell according to claim 6, wherein the recombinant cell belongs to genus *Methylacidphilum*, genus *Methylosinus*, genus *Methylocystis*, genus *Methylobacterium*, genus *Methylocella*, genus *Methylococcus*, genus *Methylomonas*, genus *Methylobacter*, genus *Methylobacillus*, genus *Methylophilus*, genus *Methylotenera*, genus *Methylovorus*, genus *Methylomicrobium*, genus *Methylophaga*, genus *Methylophilaceae*, or genus *Methyloversatilis*.

9. The recombinant cell according to claim 6, wherein the recombinant cell belongs to genus *Methanosphaera*, genus *Methanosarcina*, genus *Methanolobus*, genus *Methanococcoides*, genus *Methanohalophilus*, and genus *Methanohalobium*.

10. A method for manufacturing a recombinant cell according to claim 1, the method comprising:
    providing a host cell having the second ability to synthesize an isopentenyl diphosphate through a non-mevalonate pathway, the host cell being a *Clostridium* bacterium or a *Moorella* bacterium;
    deleting the second ability from the host cell;
    introducing the first foreign gene into the host cell; and
    introducing the second gene into the host cell.

11. A method for producing isoprene, the method comprising:
    a) bringing at least one C1 compound selected from the group consisting of carbon monoxide and carbon dioxide into contact with the recombinant cell according to claim 1, thereby allowing the recombinant cell to produce isoprene from the C1 compound.

12. The method according to claim 11, wherein the step a) comprises:
    culturing the recombinant cell using at least one C1 compound selected from the group consisting of carbon monoxide and carbon dioxide; and
    obtaining isoprene from the cultured product.

13. The recombinant cell according to claim 4, wherein the recombinant cell is an archaeon belonging to genus *Methanosarcina*, genus *Methanococcus*, or genus *Methanothermococcus*.

14. A method for producing isoprene, the method comprising:
    a) bringing at least one C1 compound selected from the group consisting of carbon monoxide and carbon dioxide into contact with a recombinant cell manufactured by the method according to claim 10, thereby allowing the recombinant cell to produce isoprene from the C1 compound.

15. The method according to claim 14, wherein the step a) comprises:
- culturing the recombinant cell using at least one C1 compound selected from the group consisting of carbon monoxide and carbon dioxide; and
- obtaining isoprene from the cultured product.

16. The recombinant cell according to claim 1, further comprising a third foreign gene encoding isopentenyl diphosphate isomerase.

\* \* \* \* \*

SEQUENCE LISTING

<160> NUMBER OF SEQ ID NOS: 10

<210> SEQ ID NO 1
<211> LENGTH: 595
<212> TYPE: PRT
<213> ORGANISM: Populus canescens

<400> SEQUENCE: 1

```
Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Phe Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Arg Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365
```

```
Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
            435                 440                 445

Pro Leu Gln Leu Ile Phe Ala Tyr Phe Ala Val Val Gln Asn Ile Lys
    450                 455                 460

Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
                500                 505                 510

Thr Lys Gly Ile Ser Glu Glu Leu Ala Thr Glu Ser Val Met Asn Leu
            515                 520                 525

Ile Asp Glu Thr Cys Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
    595

<210> SEQ ID NO 2
<211> LENGTH: 778
<212> TYPE: PRT
<213> ORGANISM: Solanum pennellii

<400> SEQUENCE: 2

Met Ile Val Gly Tyr Arg Ser Thr Ile Ile Thr Leu Ser His Pro Lys
1               5                   10                  15

Leu Gly Asn Gly Lys Thr Ile Ser Ser Asn Ala Ile Phe Gln Arg Ser
            20                  25                  30

Cys Arg Val Arg Cys Ser His Ser Thr Thr Ser Ser Met Asn Gly Phe
        35                  40                  45

Glu Asp Ala Arg Asp Arg Ile Arg Glu Ser Phe Gly Lys Leu Glu Leu
    50                  55                  60

Ser Pro Ser Ser Tyr Asp Thr Ala Trp Val Ala Met Val Pro Ser Lys
65                  70                  75                  80

His Ser Leu Asn Glu Pro Cys Phe Pro Gln Cys Leu Asp Trp Ile Ile
                85                  90                  95

Glu Asn Gln Arg Glu Asp Gly Ser Trp Gly Leu Asn Pro Thr His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140
```

```
Phe Ile Glu Thr Tyr Gly Trp Ala Val Asp Asn Lys Asp Gln Ile Ser
145                 150                 155                 160

Pro Leu Gly Phe Glu Val Ile Phe Ser Ser Met Ile Lys Ser Ala Glu
            165                 170                 175

Lys Leu Asp Leu Asn Leu Pro Leu Asn Leu His Leu Val Asn Leu Val
        180                 185                 190

Asn Cys Lys Arg Asp Ser Thr Ile Lys Arg Asn Val Glu Tyr Met Gly
        195                 200                 205

Glu Gly Val Gly Glu Leu Cys Asp Trp Lys Glu Ile Ile Lys Leu His
    210                 215                 220

Gln Arg Gln Asn Gly Ser Leu Phe Asp Ser Pro Ala Thr Thr Ala Ala
225                 230                 235                 240

Ala Leu Ile Tyr His Gln His Asp Gln Lys Cys Asn Gln Tyr Leu Asn
                245                 250                 255

Ser Ile Leu Lys Gln His Lys Asn Trp Val Pro Thr Met Tyr Pro Thr
            260                 265                 270

Lys Ile His Ser Leu Leu Cys Leu Val Asp Thr Leu Gln Asn Leu Gly
        275                 280                 285

Val His Arg His Phe Lys Ser Glu Ile Lys Lys Ala Leu Asp Glu Ile
290                 295                 300

Tyr Arg Leu Trp Gln Gln Lys Asn Glu Gln Ile Phe Ser Asn Val Thr
305                 310                 315                 320

His Cys Ala Met Ala Phe Arg Leu Leu Arg Met Ser Tyr Tyr Asp Val
                325                 330                 335

Ser Ser Asp Glu Leu Ala Glu Phe Val Asp Glu His Phe Phe Thr
            340                 345                 350

Thr Ser Gly Lys Tyr Thr Ser His Val Glu Ile Leu Glu Leu His Lys
        355                 360                 365

Ala Ser Gln Leu Ala Ile Asp His Glu Lys Asp Asp Ile Leu Asp Lys
    370                 375                 380

Ile Asn Asn Trp Thr Arg Thr Phe Met Glu Gln Lys Leu Leu Asn Asn
385                 390                 395                 400

Gly Phe Ile Asp Arg Met Ser Lys Lys Glu Val Glu Leu Ala Leu Lys
                405                 410                 415

Lys Phe Tyr Thr Thr Ser Asp Leu Ala Glu Asn Arg Arg Tyr Ile Lys
            420                 425                 430

Ser Tyr Glu Glu Asn Asn Phe Lys Ile Leu Lys Ala Ala Tyr Arg Ser
        435                 440                 445

Pro Asn Ile Asn Asn Lys Asp Leu Leu Ala Phe Ser Ile His Glu Phe
    450                 455                 460

Glu Leu Cys Gln Ala Gln His Arg Glu Glu Leu Gln Gln Leu Arg Arg
465                 470                 475                 480

Trp Phe Glu Asp Tyr Arg Leu Asp Gln Leu Gly Leu Ala Glu Arg Tyr
                485                 490                 495

Ile His Ala Thr Tyr Leu Phe Gly Val Thr Ile Ile Pro Glu Pro Glu
            500                 505                 510

Leu Ser Asp Ala Arg Leu Met Asn Ala Lys Tyr Ile Met Leu Leu Thr
        515                 520                 525

Ile Val Asp Glu Tyr Phe Glu Ser Phe Ala Ser Lys Asp Glu Cys Leu
    530                 535                 540

Asn Ile Ile Glu Leu Val Glu Arg Trp Asp Asp Tyr Ala Ser Val Gly
545                 550                 555                 560
```

```
Tyr Lys Ser Glu Lys Val Lys Val Phe Phe Ser Thr Phe Tyr Lys Ser
            565                 570                 575

Ile Glu Glu Leu Ala Thr Ile Ala Glu Ile Lys Gln Gly Arg Ser Val
        580                 585                 590

Lys Asn His Leu Ile Asn Leu Trp Leu Glu Val Met Lys Leu Met Leu
        595                 600                 605

Met Glu Gln Val Glu Trp Trp Thr Ser Lys Thr Ile Pro Ser Ile Glu
        610                 615                 620

Glu Tyr Leu Cys Val Thr Ser Ile Thr Phe Gly Ser Arg Leu Leu Leu
625                 630                 635                 640

Leu Thr Ile Gln Tyr Phe Leu Gly Ile Lys Ile Ser Lys Asp Leu Leu
                645                 650                 655

Glu Ser Asp Glu Ile Cys Gly Leu Cys Asn Cys Thr Gly Arg Val Met
            660                 665                 670

Arg Ile Leu Asn Asp Leu Gln Asp Ser Lys Arg Glu Gln Lys Gly Val
        675                 680                 685

Ser Ile Asn Leu Val Thr Leu Leu Met Lys Ser Ile Ser Glu Glu Glu
        690                 695                 700

Ala Ile Met Lys Met Lys Glu Ile Leu Glu Met Asn Arg Arg Glu Leu
705                 710                 715                 720

Leu Lys Met Val Leu Val Gln Lys Lys Gly Ser Gln Leu Pro Gln Leu
                725                 730                 735

Cys Lys Asp Ile Phe Trp Arg Thr Ser Lys Trp Thr His Phe Thr Tyr
            740                 745                 750

Ser Gln Thr Asp Gly Phe Arg Ile Glu Glu Glu Met Lys Asn His Ile
        755                 760                 765

Asp Glu Val Phe Tyr Lys Pro Leu Asn His
        770                 775

<210> SEQ ID NO 3
<211> LENGTH: 630
<212> TYPE: PRT
<213> ORGANISM: Abies grandis

<400> SEQUENCE: 3

Met Ala Leu Val Ser Ser Ala Pro Lys Ser Cys Leu His Lys Ser Leu
1               5                   10                  15

Ile Arg Ser Thr His His Glu Leu Lys Pro Leu Arg Arg Thr Ile Pro
            20                  25                  30

Thr Leu Gly Met Cys Arg Arg Gly Lys Ser Phe Thr Pro Ser Val Ser
        35                  40                  45

Met Ser Leu Thr Thr Ala Val Ser Asp Asp Gly Leu Gln Arg Arg Ile
    50                  55                  60

Gly Asp Tyr His Ser Asn Leu Trp Asp Asp Phe Ile Gln Ser Leu
65                  70                  75                  80

Ser Thr Pro Tyr Gly Glu Pro Ser Tyr Arg Glu Arg Ala Glu Lys Leu
                85                  90                  95

Ile Gly Glu Val Lys Glu Met Phe Asn Ser Met Pro Ser Glu Asp Gly
            100                 105                 110

Glu Ser Met Ser Pro Leu Asn Asp Leu Ile Glu Arg Leu Trp Met Val
        115                 120                 125

Asp Ser Val Glu Arg Leu Gly Ile Asp Arg His Phe Lys Lys Glu Ile
    130                 135                 140

Lys Ser Ala Leu Asp Tyr Val Tyr Ser Tyr Trp Asn Glu Lys Gly Ile
145                 150                 155                 160
```

```
Gly Cys Gly Arg Asp Ser Val Phe Pro Asp Val Asn Ser Thr Ala Ser
                165                 170                 175
Gly Phe Arg Thr Leu Arg Leu His Gly Tyr Ser Val Ser Ser Glu Val
            180                 185                 190
Leu Lys Val Phe Gln Asp Gln Asn Gly Gln Phe Ala Phe Ser Pro Ser
        195                 200                 205
Thr Lys Glu Arg Asp Ile Arg Thr Val Leu Asn Leu Tyr Arg Ala Ser
    210                 215                 220
Phe Ile Ala Phe Pro Gly Glu Lys Val Met Glu Ala Glu Ile Phe
225                 230                 235                 240
Ser Ser Arg Tyr Leu Lys Glu Ala Val Gln Lys Ile Pro Val Ser Ser
            245                 250                 255
Leu Ser Gln Glu Ile Asp Tyr Thr Leu Glu Tyr Gly Trp His Thr Asn
        260                 265                 270
Met Pro Arg Leu Glu Thr Arg Asn Tyr Leu Asp Val Phe Gly His Pro
    275                 280                 285
Thr Ser Pro Trp Leu Lys Lys Arg Thr Gln Tyr Leu Asp Ser Glu
290                 295                 300
Lys Leu Leu Glu Leu Ala Lys Leu Glu Phe Asn Ile Phe His Ser Leu
305                 310                 315                 320
Gln Gln Lys Glu Leu Gln Tyr Leu Ser Arg Trp Trp Ile His Ser Gly
            325                 330                 335
Leu Pro Glu Leu Thr Phe Gly Arg His Arg His Val Glu Tyr Tyr Thr
        340                 345                 350
Leu Ser Ser Cys Ile Ala Thr Glu Pro Lys His Ser Ala Phe Arg Leu
    355                 360                 365
Gly Phe Ala Lys Thr Cys His Leu Ile Thr Val Leu Asp Asp Ile Tyr
370                 375                 380
Asp Thr Phe Gly Thr Met Asp Glu Ile Glu Leu Phe Asn Glu Ala Val
385                 390                 395                 400
Arg Arg Trp Asn Pro Ser Glu Lys Glu Arg Leu Pro Glu Tyr Met Lys
            405                 410                 415
Glu Ile Tyr Met Ala Leu Tyr Glu Ala Leu Thr Asp Met Ala Arg Glu
        420                 425                 430
Ala Glu Lys Thr Gln Gly Arg Asp Thr Leu Asn Tyr Ala Arg Lys Ala
    435                 440                 445
Trp Glu Val Tyr Leu Asp Ser Tyr Thr Gln Glu Ala Lys Trp Ile Ala
450                 455                 460
Ser Gly Tyr Leu Pro Thr Phe Glu Glu Tyr Leu Glu Asn Ala Lys Val
465                 470                 475                 480
Ser Ser Gly His Arg Ala Ala Ala Leu Thr Pro Leu Leu Thr Leu Asp
            485                 490                 495
Val Pro Leu Pro Asp Asp Val Leu Lys Gly Ile Asp Phe Pro Ser Arg
        500                 505                 510
Phe Asn Asp Leu Ala Ser Ser Phe Leu Arg Leu Arg Gly Asp Thr Arg
    515                 520                 525
Cys Tyr Lys Ala Asp Arg Asp Arg Gly Glu Glu Ala Ser Ser Ile Ser
530                 535                 540
Cys Tyr Met Lys Asp Asn Pro Gly Leu Thr Glu Glu Asp Ala Leu Asn
545                 550                 555                 560
His Ile Asn Ala Met Ile Asn Asp Ile Ile Lys Glu Leu Asn Trp Glu
            565                 570                 575
```

```
Leu Leu Lys Pro Asp Ser Asn Ile Pro Met Thr Ala Arg Lys His Ala
                580                 585                 590

Tyr Glu Ile Thr Arg Ala Phe His Gln Leu Tyr Lys Tyr Arg Asp Gly
            595                 600                 605

Phe Ser Val Ala Thr Gln Glu Thr Lys Ser Leu Val Arg Arg Thr Val
        610                 615                 620

Leu Glu Pro Val Pro Leu
625             630

<210> SEQ ID NO 4
<211> LENGTH: 574
<212> TYPE: PRT
<213> ORGANISM: Artemisia annua

<400> SEQUENCE: 4

Met Ser Thr Leu Pro Ile Ser Ser Val Ser Phe Ser Ser Thr Ser
1               5                   10                  15

Pro Leu Val Val Asp Asp Lys Val Ser Thr Lys Pro Asp Val Ile Arg
                20                  25                  30

His Thr Met Asn Phe Asn Ala Ser Ile Trp Gly Asp Gln Phe Leu Thr
            35                  40                  45

Tyr Asp Glu Pro Glu Asp Leu Val Met Lys Lys Gln Leu Val Glu Glu
        50                  55                  60

Leu Lys Glu Glu Val Lys Lys Glu Leu Ile Thr Ile Lys Gly Ser Asn
65                  70                  75                  80

Glu Pro Met Gln His Val Lys Leu Ile Glu Leu Ile Asp Ala Val Gln
                85                  90                  95

Arg Leu Gly Ile Ala Tyr His Phe Glu Glu Glu Ile Glu Glu Ala Leu
            100                 105                 110

Gln His Ile His Val Thr Tyr Gly Glu Gln Trp Val Asp Lys Glu Asn
        115                 120                 125

Leu Gln Ser Ile Ser Leu Trp Phe Arg Leu Leu Arg Gln Gln Gly Phe
    130                 135                 140

Asn Val Ser Ser Gly Val Phe Lys Asp Phe Met Asp Glu Lys Gly Lys
145                 150                 155                 160

Phe Lys Glu Ser Leu Cys Asn Asp Ala Gln Gly Ile Leu Ala Leu Tyr
                165                 170                 175

Glu Ala Ala Phe Met Arg Val Glu Asp Glu Thr Ile Leu Asp Asn Ala
            180                 185                 190

Leu Glu Phe Thr Lys Val His Leu Asp Ile Ile Ala Lys Asp Pro Ser
        195                 200                 205

Cys Asp Ser Ser Leu Arg Thr Gln Ile His Gln Ala Leu Lys Gln Pro
    210                 215                 220

Leu Arg Arg Arg Leu Ala Arg Ile Glu Ala Leu His Tyr Met Pro Ile
225                 230                 235                 240

Tyr Gln Gln Glu Thr Ser His Asp Glu Val Leu Leu Lys Leu Ala Lys
                245                 250                 255

Leu Asp Phe Ser Val Leu Gln Ser Met His Lys Lys Glu Leu Ser His
            260                 265                 270

Ile Cys Lys Trp Trp Lys Asp Leu Asp Leu Gln Asn Lys Leu Pro Tyr
        275                 280                 285

Val Arg Asp Arg Val Val Glu Gly Tyr Phe Trp Ile Leu Ser Ile Tyr
    290                 295                 300

Tyr Glu Pro Gln His Ala Arg Thr Arg Met Phe Leu Met Lys Thr Cys
305                 310                 315                 320
```

```
Met Trp Leu Val Val Leu Asp Asp Thr Phe Asp Asn Tyr Gly Thr Tyr
            325                 330                 335

Glu Glu Leu Glu Ile Phe Thr Gln Ala Val Glu Arg Trp Ser Ile Ser
            340                 345                 350

Cys Leu Asp Met Leu Pro Glu Tyr Met Lys Leu Ile Tyr Gln Glu Leu
            355                 360                 365

Val Asn Leu His Val Glu Met Glu Glu Ser Leu Glu Lys Glu Gly Lys
            370                 375                 380

Thr Tyr Gln Ile His Tyr Val Lys Glu Met Ala Lys Glu Leu Val Arg
385                 390                 395                 400

Asn Tyr Leu Val Glu Ala Arg Trp Leu Lys Gly Tyr Met Pro Thr
            405                 410                 415

Leu Glu Glu Tyr Met Ser Val Ser Met Val Thr Gly Thr Tyr Gly Leu
            420                 425                 430

Met Ile Ala Arg Ser Tyr Val Gly Arg Gly Asp Ile Val Thr Glu Asp
            435                 440                 445

Thr Phe Lys Trp Val Ser Ser Tyr Pro Pro Ile Ile Lys Ala Ser Cys
            450                 455                 460

Val Ile Val Arg Leu Met Asp Asp Ile Val Ser His Lys Glu Glu Gln
465                 470                 475                 480

Glu Arg Gly His Val Ala Ser Ser Ile Glu Cys Tyr Ser Lys Glu Ser
            485                 490                 495

Gly Ala Ser Glu Glu Glu Ala Cys Glu Tyr Ile Ser Arg Lys Val Glu
            500                 505                 510

Asp Ala Trp Lys Val Ile Asn Arg Glu Ser Leu Arg Pro Thr Ala Val
            515                 520                 525

Pro Phe Pro Leu Leu Met Pro Ala Ile Asn Leu Ala Arg Met Cys Glu
            530                 535                 540

Val Leu Tyr Ser Val Asn Asp Gly Phe Thr His Ala Glu Gly Asp Met
545                 550                 555                 560

Lys Ser Tyr Met Lys Ser Phe Phe Val His Pro Met Val Val
            565                 570
```

<210> SEQ ID NO 5
<211> LENGTH: 857
<212> TYPE: DNA
<213> ORGANISM: Staphylococcus aureus

<400> SEQUENCE: 5

```
aaagagggtt ataatgaacg agaaaaatat aaaacacagt caaaacttta ttacttcaaa    60
acataatata gataaaataa tgacaaatat aagattaaat gaacatgata atatctttga   120
aatcggctca ggaaaagggc attttaccct tgaattagta cagaggtgta atttcgtaac   180
tgccattgaa atagaccata aattatgcaa aactacagaa ataaacttg ttgatcacga    240 taatttccaa gttttaaaca aggatatatt gcagtttaaa tttcctaaaa accaatccta   300
taaaatattt ggtaatatac cttataacat aagtacggat ataatacgca aaattgtttt   360
tgatagtata gctgatgaga tttatttaat cgtggaatac gggtttgcta aaagattatt   420
aaatacaaaa cgctcattgg cattattttt aatggcagaa gttgatattt ctatattaag   480
tatggttcca agagaatatt ttcatcccta acctaaagtg aatagctcac ttatcagatt   540
aaatagaaaa aaatcaagaa tatcacacaa agataaacag aagtataatt atttcgttat   600
gaaatgggtt aacaaagaat acaagaaaat atttacaaaa aatcaattta acaattcctt   660
```

| | | |
|---|---|---|
| aaaacatgca ggaattgacg atttaaacaa tattagcttt gaacaattct tatctctttt | 720 | |
| caatagctat aaattattta ataagtaagt taagggatgc ataaactgca tcccttaact | 780 | |
| tgtttttcgt gtacctattt tttgtgaatc gattatgtct tttgcgcatt cacttctttt | 840 | |
| ctatataaat atgagcg | 857 | |

```
<210> SEQ ID NO 6
<211> LENGTH: 5510
<212> TYPE: DNA
<213> ORGANISM: Artificial
<220> FEATURE:
<223> OTHER INFORMATION: Plasmid pUC-dxr-ermC

<400> SEQUENCE: 6
```

| | | |
|---|---|---|
| gacgaaaggg cctcgtgata cgcctatttt tataggttaa tgtcatgata ataatggttt | 60 | |
| cttagacgtc aggtggcact tttcggggaa atgtgcgcgg aacccctatt tgtttatttt | 120 | |
| tctaaataca ttcaaatatg tatccgctca tgagacaata accctgataa atgcttcaat | 180 | |
| aatattgaaa aaggaagagt atgagtattc aacatttccg tgtcgccctt attccctttt | 240 | |
| ttgcggcatt ttgccttcct gttttttgctc acccagaaac gctggtgaaa gtaaaagatg | 300 | |
| ctgaagatca gttgggtgca cgagtgggtt acatcgaact ggatctcaac agcggtaaga | 360 | |
| tccttgagag ttttcgcccc gaagaacgtt ttccaatgat gagcactttt aaagttctgc | 420 | |
| tatgtggcgc ggtattatcc cgtattgacg ccgggcaaga gcaactcggt cgccgcatac | 480 | |
| actattctca gaatgacttg gttgagtact caccagtcac agaaaagcat cttacggatg | 540 | |
| gcatgacagt aagagaatta tgcagtgctg ccataaccat gagtgataac actgcggcca | 600 | |
| acttacttct gacaacgatc ggaggaccga aggagctaac cgcttttttg cacaacatgg | 660 | |
| gggatcatgt aactcgcctt gatcgttggg aaccggagct gaatgaagcc ataccaaacg | 720 | |
| acgagcgtga caccacgatg cctgtagcaa tggcaacaac gttgcgcaaa ctattaactg | 780 | |
| gcgaactact tactctagct tcccggcaac aattaataga ctggatggag gcggataaag | 840 | |
| ttgcaggacc acttctgcgc tcggcccttc cggctggctg gtttattgct gataaatctg | 900 | |
| gagccggtga gcgtgggtct cgcggtatca ttgcagcact ggggccagat ggtaagccct | 960 | |
| cccgtatcgt agttatctac acgacgggga gtcaggcaac tatggatgaa cgaaatagac | 1020 | |
| agatcgctga gataggtgcc tcactgatta agcattggta actgtcagac caagtttact | 1080 | |
| catatatact ttagattgat ttaaaacttc atttttaatt taaaaggatc taggtgaaga | 1140 | |
| tcctttttga taatctcatg accaaaatcc cttaacgtga gttttcgttc cactgagcgt | 1200 | |
| cagaccccgt agaaaagatc aaaggatctt cttgagatcc ttttttctg cgcgtaatct | 1260 | |
| gctgcttgca acaaaaaaa ccaccgctac cagcggtggt ttgtttgccg gatcaagagc | 1320 | |
| taccaactct ttttccgaag gtaactggct tcagcagagc gcagatacca aatactgttc | 1380 | |
| ttctagtgta gccgtagtta ggccaccact caagaactc tgtagcaccg cctacatacc | 1440 | |
| tcgctctgct aatcctgtta ccagtggctg ctgccagtgg cgataagtcg tgtcttaccg | 1500 | |
| ggttggactc aagacgatag ttaccggata aggcgcagcg gtcgggctga cggggggtt | 1560 | |
| cgtgcacaca gcccagcttg gagcgaacga cctacaccga actgagatac ctacagcgtg | 1620 | |
| agctttgaga aagcgccacg cttcccgaag ggagaaaggc ggacaggtat ccggtaagcg | 1680 | |
| gcagggtcgg aacaggagag cgcacgaggg agcttccagg gggaaacgcc tggtatcttt | 1740 | |
| atagtcctgt cgggtttcgc cacctctgac ttgagcgtcg atttttgtga tgctcgtcag | 1800 | |
| gggggcggag cctatggaaa aacgccagca acgcggcctt tttacggttc ctggccttt | 1860 | |

```
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgaattcctt aagagtagag gcaaattata aatttgtatt ttttgctatt    2280
atagtgtcaa ttttttatggc gctttgtatt ccagttttag atgtggaata taattttttta   2340 gatgtagcaa ctaccttgtt tggttttcta tatgtggcag tatttttag cactatagtt     2400 ttagtaaata gcagtagtta tggtaactat ttagtgtgga ttatagttat atcttcctgg    2460
tgctgtgata cagcagctta ttatacgggt aagttttag gtaagaaaaa attatgtcct     2520
aaggtgagtc ctaaaaagac tgtggaaggt tctataggtg gaataattgg tagtgcagtg   2580
gcttgtggaa tctttggatt ttttcaatt caaagggtg ttcctatatc attttatcat      2640
tatatagtaa tgggagtaat ttgtggagca ttttgtcagt tcggggattt agcagcttct    2700
tctataaaga gatatgttgg agtaaaggac tatagcaacc ttataccagg tcatggtggg    2760
atcttagata gatttgacag catactttt tcaggagtta tagtttatta ttatctaacc     2820
tttgtagctg taatttaagt agcgaaccca atctctgat ttggtgtgag tcacttactc     2880
attcgaccca agggagaagg agttacataa attagaaccc aaatcctaac aagttaagaa   2940
ttaataatga aaagttaata gtgaaggatg atttttagct atcgcaaaaa atctacatta    3000
actattaatt aaaaaatt tacatgtgcg aaagttgagt taataataga gaaatatatt     3060
ctataaaaag gatatgtttc tctattattt tatttcatgt attagctgtg agtttaatat    3120
agatcatgtg cgtatttatt ttatagcata aatatggtat agttaatcat gttaaaaatc    3180
ttaaaaatct tatttaatgt gttataagga ctagaggaaa atgaggagtt gttatgagga   3240 tccaagagg gttataatga acgagaaaaa tataaaacac agtcaaaact ttattacttc     3300
aaaacataat atagataaaa taatgacaaa tataagatta aatgaacatg ataatatctt    3360
tgaaatcggc tcaggaaaag ggcatttttac ccttgaatta gtacagaggt gtaatttcgt   3420
aactgccatt gaaatagacc ataaattatg caaaactaca gaaaataaac ttgttgatca    3480
cgataatttc caagttttaa acaaggatat attgcagttt aaatttccta aaaaccaatc    3540
ctataaaata tttggtaata taccttataa cataagtacg gatataatac gcaaaattgt    3600
ttttgatagt atagctgatg agatttattt aatcgtggaa tacgggtttg ctaaaagatt    3660
attaaataca aaacgctcat tggcattatt tttaatggca gaagttgata tttctatatt    3720
aagtatggtt ccaagagaat attttcatcc taaacctaaa gtgaatagct cacttatcag    3780
attaaataga aaaaaatcaa gaatatcaca caaagataaa cagaagtata attatttcgt    3840
tatgaaatgg gttaacaaag aatacaagaa aatatttaca aaaaatcaat ttaacaattc    3900
cttaaaacat gcaggaattg acgatttaaa caatattagc tttgaacaat tcttatctct    3960
tttcaatagc tataaattat ttaataagta agttaaggga tgcataaact gcatcccta    4020 acttgttttt cgtgtaccta tttttgtga atcgattatg tctttgcgc attcacttct      4080 tttctatata aatatgagcg gtcgacgaat tgggaggaat accatttgta tataatagca    4140
gcgataatag cctttggcgt attgattata attcatgaac tgggacatt tactatggcg     4200
```

```
aaattaaatg gagtaaaagt agaagaattt tctataggaa tgggtcctaa gctctttgga    4260
ataaagggca aggaaacgga atatcatata aggcttcttc ctattggtgg ttatgtaaag    4320
atgctgggtg atgagggtga aagtgatgac cctagggcat ttaataataa aagtcctctt    4380
agaaaactta gtgtagtaac agctggaccc ataatgaatt ttgtacttgg agttatacta    4440
tttgcaataa tagcttctgc gagggggtat ctgtctccta tagtgagtaa agtaatgcca    4500
aatcaacctg cagctttagc gggtataaag ctaggagata aaataactag ggtaaataat    4560
tcaaagatat ctacctggga agactttgta acagaagttt atactgcagg aggaaatcca    4620
attaatataa cttatgaacg taatggaaac acaaatcagg taagagttat tccaataaaa    4680
gataaaaaag aaaataggta tgttgtaggt attgaatcaa ctcaagtcac taagcctact    4740
ttggggcagt cagtatccta tgggtttata gaaactaaat ccctaatcaa gcagacattt    4800
agttttttta aaacactatt tagaggaaaa gcatctatga atgatgtagg gggacctgtt    4860
actataataa aaatatcagg tgcagcagca aaagcaggaa tattgagttt gatggcattt    4920
tcagcttata taagtataca gcttgctata tttaacataa tacctttttcc agctttggat    4980 ggaggatata tattttttatt tttgtttgaa ataataacag gtaaaaaagt agatgaaaat    5040
aaggttggaa cgataaatta tgttggattt gcaatactta tggcacttat ggtactagtt    5100
accgtaaagc ttggcactgg ccgtcgtttt acaacgtcgt gactgggaaa accctggcgt    5160
tacccaactt aatcgccttg cagcacatcc ccctttcgcc agctggcgta atagcgaaga    5220
ggcccgcacc gatcgccctt cccaacagtt gcgcagcctg aatggcgaat ggcgcctgat    5280
gcggtatttt ctccttacgc atctgtgcgg tatttcacac cgcatatggt gcactctcag    5340
tacaatctgc tctgatgccg catagttaag ccagccccga cacccgccaa cacccgctga    5400
cgcgccctga cgggcttgtc tgctcccggc atccgcttac agacaagctg tgaccgtctc    5460
cgggagctgc atgtgtcaga ggttttcacc gtcatcaccg aaacgcgcga             5510
```

<210> SEQ ID NO 7
<211> LENGTH: 3983
<212> TYPE: DNA
<213> ORGANISM: Lactobacillus johnsonii

<400> SEQUENCE: 7

```
taaaagattg ctaagattgt ttagcaatct ttttttagaa ttgattaaaa aaattatact      60
ttatacattt gatgcatggc gtgagctatc atgttaatag aataattttt attaagaggt     120
ggaagagtgt tacaggatgt ttatatagta ggaatgaatc gaattccttt tggtaagtat     180
cgtggatttt ataaggataa aagtgctgtt gacctaggag tgttagcact aagggatta     240 ttgaaaaaga atattgttcc acaagataaa atagatagca ttttggtggg aaatgtatta     300
agtgctgggc taggtcaaaa tgtcgctcga caaatagctt aaaatcagg tttacctgaa     360 tctgtagtgg gtactagcgt agacgacgtt tgtggttcaa gtttaaaggc attacgtttt     420
gctcaaggtc aaatgctcct aggagattct caaattgcaa ttgtaggtgg ggcagaaagt     480
atgacaaatg caccactttt acttgataaa agtaaaaagc atgatgaaaa tccagcatat     540
caagatagct taatgataga tggaattggg atgcttattt cgagaaagcc gatgggaatt     600
acagctgaga atgtagctga taaataccat attacgcgtc aagatatgga tgaatttgca     660
cgtgattctc atgccaaggc ttatgcagct caggagaatg actggtttaa ggaagagtat     720
gcaccaattg aactcgatgg tcatgttctt gatcatgatg aaaccattcg accagattct     780
agtttagaag ccctaggtca attaaaacct gtatttaagg aaaatggacg agttacggct     840
```

```
ggcaattctt caccgttaac tgatggtgca agtatgttgt tattatctaa tcaacaaaaa    900
ttagatgaat taaatttaac tccattagca tacttgggtg cctatgcaga aattggctgt    960
gatcctgctt atatgggata cgcaccatat tttgctatta aaaaattact tacaaaaact   1020
aatagcacaa ttgaggatta tgatctaatt gaaattaatg aggcctttgc agctcaagca   1080
tatgctgtag cccgtgatct aaatattcca aaagaaaaat aaatatcgc tggaggagca   1140 attagtttag gacatccgct tggtgcaacc ggtacgcgct tagtaatgag tgcagtaaac   1200
agtttgcgta aaattaatgg tcgaagagca attgtatctc tatgtattgg cggtggccaa   1260
ggaatcgcat atgaaattag aagaatcatc taaaaagaaa ttttatcaat ggttaccaga   1320
ggaaagaaga gtcttttaa ctgaaaaagg aattaaacta agtgagattg agtctgaaac   1380
tttggaaaga ctagataaac ttagtgaaaa tgtaattggt caagtccgtc ttcctcttgg   1440
tgtgcttcct aagttaatag ttaacgggaa agattatcaa gtaccaatgg ccgtagaaga   1500
accatcggtt gttgcagcag caaaccatgc agctaaaatt tttaatcaaa atggtggagc   1560
agtagctgat agtagacgaa atggaatata tggtcaaatt gttttagagg taactgataa   1620
ttttgattta actaagttta ctactgaatt tcctcaatta attagcttag ctaataaaaa   1680
attcgttagc ttagtcaagc atggtggagg agttcgtaaa attgaagctt ctcaaaaaga   1740
aaatttagtt tttcttagag ttttggttga cccagcagaa gctatgggag ctaataaaac   1800
aaatgctatt ttagaatttt taggaaatga attagagaag cagccagata ttgaacaaac   1860
tctgtatgca attttgtcta attatcctac gcaattgact agtgctaaag taagtctttc   1920
aattgacagt gtaggaggat taaagttgc taaaaagata gctttattga gtaaaatagg   1980
acaaactgat atttaccggg cagtgactaa taataaagga attatgaatg gtattgatag   2040
tgtattggtt gcaactggta atgattatcg tggagttgaa gcagcaactg ctgtttgggc   2100
taataaaaat ggtgcctata catctttgag taagtggaaa attgaagaag atagactagt   2160
ggggactgta acagttccct tagcaatcgg tgtagtaggt ggctcaatta aggctcgtcg   2220
agacgttcaa caaagcttta gtttattagg taatatatct gccaagcaac tagcagaagt   2280
tattgcgaca actggcttag caaataactt ttcagctctt ttagcaattt ctactaaggg   2340
aattcaagct gggcatatga aattgcaggc gagaaattta gtagcaacct taaaagctag   2400
tgaaggtgaa aaagcaatag ttttaaaaaa attgcaggaa agtaaaaaat atactcaaga   2460
agcagctttt gaatttttaa gcgaaataag aaaggatcaa aataagatg aaggttggaa   2520 ttgatcaaat tggatatttt actccaaata agtatgttga tatggtggat ttagcccatg   2580
ctaggaatca agatccaaat aaattttaa ttgggattgg acagaaaaaa atgagcgttg   2640
cagatccaac tcaagatgca gtttcaatgg gaattaatgc aactctacgc tatatcgata   2700
agattgataa atcaaaagta ggacttttga ttttggtac tgaaagtagt gtggatcaat   2760
ctaaatctgg ctctttattt gtaaaatcgg cattagggtt agatcctact gtgagagctt   2820
ttgaagttaa ggaagcatgt tttggcttaa cggctggctt aatgattgcc caagattttg   2880
tacgacttca tcctgatcaa actgctattg ttatcggcag tgatattgct cgctatgggg   2940
ttaatactgc tggtgaagtt actcaaggag ctggaagtgt tagtttatta atttctagta   3000
atccaagaat tttagaatta aatgaaggcc atagtgctta tagtgaggat atcaatgatt   3060
tctggcgccc taactattct aaaacagcca aggtagatgg aaagtattct acccaggttt   3120
acttagactt tttcaaacat acttttttctg cttacaaaga acaaaagaat cttgaaacaa   3180
```

```
aagatttttgc cgctattgtc taccacttac cttttactaa gatgggatta aaggcaaata    3240
gattagctgt tgagggaacg gatgaagaaa caaatgcccg gttaatggac agctttactg    3300
cagctaaaga attgaatgca aatgtaggta atatttacac tggatcgtta tacttgagtc    3360
tacttagttt acttgaaaat ggtaggttaa aagctggaga cttagtcggt ctattttctt    3420
atggttcagg tgcaatggct gaattttatt ccgcaaatgt agttgaaggc tatgaaaaac    3480
aacttgataa ggttggagat aaagctttat tagataatcg aagcaagctt agtgttgccg    3540
aatatgagga atctttttct gcaggtttgg aagatccaga aaacaatgtt gaacttatca    3600
gtgatgaaga aactggtaga tattattttg ctggtattcg taatgatatc cgccaatatc    3660
aagttaaata acttgtattc gcttacatag ttgttataat aagatgtgtg gagaggtaga    3720
ataatattgt aaatagtttt tatctccaga ttgtagtgtt ttaaagacaa gattctctta    3780
gtaagatcaa atagtcgtta ttcaatacag atgcaaacaa gtgatgttga tcaagtcata    3840
atatcaaacc cagatactga cgttatggcg ctagatagta tttacctcat ccacttgaaa    3900
aaaggttgta gaccaggcag tctacaacct ttttataag cacaaaaaag cagtcacatc     3960
gactgcttaa attaatataa tta                                            3983
```

<210> SEQ ID NO 8
<211> LENGTH: 4313
<212> TYPE: DNA
<213> ORGANISM: Lactobacillus johnsonii

<400> SEQUENCE: 8

```
cataagtctc tagtctcctt agcaaatatt ttagcatatg agacaaggca attagactta      60
atgaaattta aatataggaa agataattg tgaataaaaa aatagaagtc aaagcacatg      120
gaaaagtgat tcttattggt gagcattctg tagtttatgg ctatgatgcc ctcgctcttc      180
caatccaggc cttaaatatc accacaactg ttgaagaaac tgatggtcct acttggatgg      240
atacaactca ttatcatggt gcttttttg atgcgccgga tgaatacgat ggtattaaat       300
atattgtgaa aactttactt gaaagagtag aaaacgctcc taatcttaaa attacttata      360
ctggtgaaat tcctatggaa cggggttttg gatcaagtgc tgttgtagct ttaggaacta      420
ccaaggctgt ttcacaattt ttaggattaa ctctttctga agctgagatc atggaaatca      480
ctaatcatgc agaaatgatt aatcatggaa aagcttccgg ccttgacgct gctaccgtaa      540
attccgatta cttagttttc ttcaataaac aagacggacc aaaacagctt tctcaaaaat      600
taggtgctac cttattaatt atggatacgg gtgaacttgg aaataccaaa gtcgcagttc      660
aatcagttaa aaagcaaatg gatgaaagtg atcttaaaaa gaaacaaatt gcacggcttg      720
gagaattagc taccgcaaca cgacaaaatt ggtttaacca aaatgcagaa gagatcggga      780
agatttttaa tgaagccgaa gacatccttg cctccttta gctttcaact gaaagaatcg       840
ataatatttg taaattgcc aatgaaaatg gcgctttagg agctaaatta tctggtggtg       900
gcttaggtgg cattgtaatt gcactatgtc ctaatcaaga agttgctaaa aaaattgccg      960
aaaaagctaa agctaatttt gataatgact ggattgagga atttaatga agaaaactgc      1020 tcgtgcccac actaatatcg ccttaattaa atattgggga aaagctgacc aagctttaaa     1080
gacaccgtta atgtctagtc tttcaatgac attagatgcc ttttatactg atactacatt     1140
tgaacatgat tcctcattaa ctgaagatac ctttatttta aatgatcaaa acaatcagt      1200 agaagacagc aagcgagttt ttaattatat tcatttatta caagaaaagt ttggcgttaa     1260
tgaccacttt acaattcggt ctacaaacca tgttcctact tctgctggcc ttgcttcctc      1320
```

-continued

```
agcatcagct tttgcggctc ttgcaacaag ctttgttgca agctatggat tagatctttc    1380
taaaaaggag ctttcaagac ttgcacgcct tgggtctggg tcagcgacta gatcagttta    1440
tggcggcttt gttgaatgga aaaaggatt tgatgatgag agctcctatg cagctccaat     1500
tgatgaaaat cctgatcttg atctttctct actagcaatc gaagttaata caaagcagaa    1560
aaaaatttct tcaacaaaag gaatgcagtt agcccaaacc tctccttttt atcaaccttg    1620
gttagctaga acgaagaag aaattgctga aattaaacaa gctatccaaa ataatgactt     1680
tactagaatt ggtgaactta gtgaactaag tgccaacgag atgcacgctt gcaatttaac    1740
tgctaaagaa ccctttactt attttgaacc ggaaacaatt aaaattatta aattagttga    1800
agatttaaga aaaaatggca tcgaatgtta ctatacaatt gatgctggtc aaacgtaaa    1860 aattctctgc accttaagaa atagaaaaga tattatttca gctgttcaga aaaccttgac    1920
taatgttaaa atagtcgttg cgagtttcgg cccaggcgtt actctgcttt agtaatttga    1980
aaataaaaag attagaggaa tattcgttga ttacagaaca agcaccagga aagttgtata    2040
ttgcgggaga gtatgcagtt cttgagcaaa actgccctgc cattttagtt gcagtaaatg    2100
aatttgtacg tgtttcaatt gcaaagagta caggtacaag tgggttaatt cattctaaac    2160
agtattctca agattcaatt cactggatcc gtaaaggtaa ccaaatggtt attgataatc    2220
gtgataatcc gtttgaatac attttatctg ctattaactt tacagaacgt ttttgtcttg    2280
aacaaaaagt ttcaatgtct ttatatgacc tacatgttaa ttcagatctt gattcagccg    2340
acggtaaaaa atacggtctt ggctcttcag cggctgtaac agttgctacg gtgaaggcta    2400
ttcttaattt ctatggatta cactgtacaa aagatcttat ttttaaactt tctgctattt    2460
ctcactatag cgttcaaggt aatggttctg ctggtgatat tgcagcaagt gtttacggtg    2520
gttggcttgc ttatcaaact tttgataaag catggcttaa gaaagaatta gctactaaat    2580
ctcttagcga agttttaaat gaagcttggc ctggtcttaa gattcaatta ttaactcctc    2640
cagaaggact aaacttggta attggttgga gtcaaaagcc tgcttcaact tctcaattag    2700
ttgataaaac taatgcaaag aaaaagttta ttaagactca atatgacact tttttagatg    2760
aatcacggaa atgtgttctt gatatgatta agggctttaa tgaaaaaaat atttctttaa    2820
ttcaaaaaca aattcgttta aatcgtcagt tattaaaaga ctttgcttct cttaaccata    2880
ttgctatcga aatcccacgt ttaactaaat taattatat tgccgaacaa tttaatggcg    2940
ctgctaagac ttctggtgca ggaaatggcg attgtggtat tgtgattgca gatgaaaaaa    3000
ctgatatcga agaaatgaaa aataattggc gtaaaatgg aattatgcca ttgaactttc     3060
tagttcactc aattgcttag tgggaaaaat tatgtcacaa agatctcaaa gaaaagaaga    3120
acatctagca ttagctaaga tgttttttaa tagtaataaa gataatgatt ttaatcatgt    3180
tcatttaatc cgccctgctc ttccagaaag tgcaataagt agagatagta tttcaactga    3240
aatgtttggt catactatca gtactcccctt ctttattaat gcaatgactg gcggctctga    3300
tacttcctat accatcaatc aacgtttagc taaagcggct gccgcagaaa atattccgat    3360
ggctttagga tccgctagca ttcttgaaaa agaaattgat caaatagaga gctttgaagt    3420
tgcacgtcaa gaaaatcctg atggactaat ttttgcaaat gttaatccaa ctactgatcc    3480
aaaagtagct caaaagattg ttgacgcttt agatgcaaat gcattacaga ttcatcttaa    3540
tagtgttcaa gaagctgtaa tgcctgaagg cgatcgagat tttcattgga tagataatct    3600
aaaagaaatt agagatacag ttgatgtgcc aattattatt aaagaagttg gaatgggaat    3660
```

| | |
|---|---|
| tgatcctgaa tctcttcgta ccctttaat caatgacttt tcaattatcg atttaggtgg | 3720 |
| aagtggcgga actaatttg cgcaaattga aaatgaaaga cgaaagactc aaaaattaaa | 3780 |
| cttttagaa gatattggtc tttctactgt taaaacgctg cttgcagcac gcactatccc | 3840 |
| tgttaataaa actattattg cagctggtgg cattacaaat gcactggaca tttttaagtc | 3900 |
| tttagtttta ggtgcacagt atgttggtat tgcaaactat ttcttgcagt atgctagcca | 3960 |
| agattccgag actttgattg ctgctattca aaacttaaaa tatgaattga aactttaac | 4020 |
| tgctctattt ggtttagatc atatttctaa agccgatgaa gttagatatt atttggatac | 4080 |
| tgatctttac aatttcactc gacaactcta aattagtgc tatttcgttg gatggctgct | 4140 |
| ataagcagcc atccttttg ttttattat tttttaaatg ttaaagtaac aatttatta | 4200 |
| atttaaatat aaaagtaaa aaagttcatt aaattaaatt tggatcaata ccaaaagtta | 4260 |
| atttaatgaa cttcgttcta ctaaataaca aaagctaatt aataatgttt tta | 4313 |

<210> SEQ ID NO 9
<211> LENGTH: 1788
<212> TYPE: DNA
<213> ORGANISM: Populus canescens

<400> SEQUENCE: 9

| | |
|---|---|
| atggcaactg aattattgtg cttgcaccgt ccaatctcac tgacacacaa attgttcaga | 60 |
| aatcccttgc ctaaagtcat ccaggccact cccttaactt tgaaactcag atgttctgta | 120 |
| agcacagaaa acgtcagctt cacagaaaca gaaacagaaa ccagaaggtc tgccaattat | 180 |
| gaaccaaata gctgggatta tgattatttg ctgtcttcgg acactgacga atcgattgaa | 240 |
| gtatacaaag acaaggccaa aaagctggag gctgaggtga aagagagat taacaatgaa | 300 |
| aaggcagagt ttttgactct gcctgaactg atagataatg tccaaggtt aggattaggt | 360 |
| taccggttcg agagtgacat aaggagagcc cttgatagat ttgtttcttc aggaggattt | 420 |
| gatgctgtta caaaaactag ccttcatgct actgctctta gcttcaggct tctcagacag | 480 |
| catggctttg aggtctctca agaagcgttc agcggattca aggatcaaaa tggcaatttc | 540 |
| ttgaaaaacc ttaaggagga catcaaggca atactaagcc tatatgaagc ttcattct | 600 |
| gccttagaag gagaaatat cttggatgag gccaaggtgt tgcaatatc acatctaaaa | 660 |
| gagctcagcg aagaaaagat tggaaaagac ctggccgaac aggtgaatca tgcattggag | 720 |
| cttccattgc atcgaaggac gcaaagacta gaagctgttt ggagcattga agcataccgt | 780 |
| aaaaaggaag atgcagatca agtactgcta gaacttgcta tattggacta caacatgatt | 840 |
| caatcagtat accaaagaga tcttcgcgag acatcaaggt ggtggaggcg tgtgggtctt | 900 |
| gcaacaaagt tgcattttgc tagagacagg ttaattgaaa gcttttactg ggcagttgga | 960 |
| gttgcgtttg aacctcaata cagtgattgc cgtaattccg tagcaaaaat gttttcgttt | 1020 |
| gtaacaatca ttgatgatat ctatgatgtt tatggtactc tggatgagtt ggagctattt | 1080 |
| acagatgctg ttgagagatg ggatgttaat gccatcgatg atcttccgga ttatatgaag | 1140 |
| ctctgcttcc tagctctcta taacactatc aatgagatag cttatgataa tctgaaggac | 1200 |
| aaggggggaaa acattcttcc ataccctaaca aaagcgtggg cagatttatg caatgcattc | 1260 |
| ctacaagaag caaaatggtt gtacaataag tccacaccaa catttgatga atatttcgga | 1320 |
| aatgcatgga atcatcctc agggcctctt caactagtttt ttgcctactt tgccgttgtt | 1380 |
| caaaacatca gaagagga aattgataac ttacaaagt atcatgatat catcagtagg | 1440 |
| ccttcccaca tctttcgtct ttgcaacgac ttggcttcag catcggctga gatagcgaga | 1500 |

```
ggtgaaaccg cgaattctgt atcatgctac atgcgtacaa aaggcatttc tgaggaactt    1560
gctactgaat ccgtaatgaa tttgatcgac gaaacctgga aaaagatgaa caagaaaag     1620 cttggtggct ctctgtttgc aaaacctttt gtcgaaacag ctattaacct tgcacgacaa    1680
tcccattgca cttatcacaa cggagatgcg catacttcac cagatgagct cactaggaaa    1740
cgtgtcctgt cagtaatcac agagcctatt ctacccttg agagataa                  1788

<210> SEQ ID NO 10
<211> LENGTH: 16228
<212> TYPE: DNA
<213> ORGANISM: Artificial
<220> FEATURE:
<223> OTHER INFORMATION: Plasmid pSK1(LbMVA-ISPS)

<400> SEQUENCE: 10
gaattcgagc tcggtacctt tttaacaaaa tatattgata aaaataataa tagtgggtat     60
aattaagttg ttagagaaaa cgtataaatt agggataaac tatggaactt atgaaataga    120
ttgaaatggt ttatctgtta ccccgtagtg ttacaggatg tttatatagt aggaatgaat    180
cgaattcctt ttggtaagta tcgtggattt tataaggata aaagtgctgt tgacctagga    240
gtgttagcac ttaagggatt attgaaaaag aatattgttc cacaagataa aatagatagc    300
attttggtgg gaaatgtatt aagtgctggg ctaggtcaaa atgtcgctcg acaaatagct    360
ttaaaatcag gtttacctga atctgtagtg gtactagcg tagacgacgt tgtggttca     420 agtttaaagg cattacggtt tgctcaaggt caaatgctcc taggagattc tcaaattgca    480
attgtaggtg gggcagaaag tatgacaaat gcaccacttt tacttgataa agtaaaaag    540 catgatgaaa atccagcata tcaagatagc ttaatgatag atggaattgg ggatgcttat    600
tcgagaaagc cgatgggaat tacagctgag aatgtagctg ataaatacca tattacgcgt    660
caagatatgg atgaatttgc acgtgattct catgccaagg cttatgcagc tcaggagaat    720
gactggttta aggaagagta tgcaccaatt gaactcgatg gtcatgttct tgatcatgat    780
gaaaccattc gaccagattc tagttttaga agccctaggt caattaaaac tgtatttaag    840
gaaaatggac gagttacggc tggcaattct tcaccgttaa ctgatggtgc aagtatgttg    900
ttattatcta atcaacaaaa attagatgaa ttaaatttaa ctccattagc atacttgggt    960
gcctatgcag aaattggctg tgatcctgct tatatgggat acgcaccata ttttgctatt   1020
aaaaaattac ttacaaaaac taatagcaca attgaggatt atgatctaat tgaaattaat   1080
gaggcctttg cagctcaagc atatgctgta gcccgtgatc taaatattcc aaaagaaaaa   1140
ttaaatatcg ctggaggagc aattagttta ggacatccgc ttggtgcaac cggtacgcgc   1200
ttagtaatga gtgcagtaaa cagtttgcgt aaaattaatg gtcgaagagc aattgtatct   1260
ctatgtattg gcggtggcca aggaatcgca tatgaaatta aagaatcat ctaaaaagaa    1320 atttttatcaa tggttaccag aggaaagaag agtctttta actgaaaaag gaattaaact   1380
aagtgagatt gagtctgaaa ctttggaaag actagataaa cttagtgaaa atgtaattgg   1440
tcaagtccgt cttcctcttg gtgtgcttcc taagttaata gttaacggga aagattatca   1500
agtaccaatg gccgtagaag aaccatcggt tgttgcagca gcaaaccatg cagctaaaat   1560
ttttaatcaa aatggtggag cagtagctga tagtagacga aatggaatat atggtcaaat   1620
tgttttagag gtaactgata ttttgatttt aactaagttt actactgaat tcctcaatt    1680 aattagctta gctaataaaa aattcgttag cttagtcaag catggtggag gagttcgtaa   1740
```

```
aattgaagct tctcaaaaag aaaatttagt ttttcttaga gttttggttg acccagcaga    1800
agctatggga gctaataaaa caaatgctat tttagaattt ttaggaaatg aattagagaa    1860
gcagccagat attgaacaaa ctctgtatgc aattttgtct aattatccta cgcaattgac    1920
tagtgctaaa gtaagtcttt caattgacag tgtaggagga ttaaaagttg ctaaaaagat    1980
agctttattg agtaaaatag acaaactga  tatttaccgg gcagtgacta ataataaagg    2040
aattatgaat ggtattgata gtgtattggt tgcaactggt aatgattatc gtggagttga    2100
agcagcaact gctgtttggg ctaataaaaa tggtgcctat acatctttga gtaagtggaa    2160
aattgaagaa gatagactag tggggactgt aacagttccc ttagcaatcg gtgtagtagg    2220
tggctcaatt aaggctcgtc gagacgttca acaaagcttt agtttattag gtaatatatc    2280
tgccaagcaa ctagcagaag ttattgcgac aactggctta gcaaataact tttcagctct    2340
tttagcaatt tctactaagg gaattcaagc tgggcatatg aaattgcagg cgagaaattt    2400
agtagcaacc ttaaaagcta gtgaaggtga aaaagcaata gttttaaaaa aattgcagga    2460
aagtaaaaaa tatactcaag aagcagcttt tgaattttta agcgaaataa gaaggatca    2520 aaaataagat gaaggttgga attgatcaaa ttggatattt tactccaaat aagtatgttg    2580
atatggtgga tttagcccat gctaggaatc aagatccaaa taaatttta attgggattg    2640 gacagaaaaa aatgagcgtt gcagatccaa ctcaagatgc agtttcaatg ggaattaatg    2700
caactctacg ctatatcgat aagattgata atcaaaagt aggactttg attttggta    2760 ctgaaagtag tgtggatcaa tctaaatctg gctctttatt tgtaaaatcg gcattagggt    2820
tagatcctac tgtgagagct tttgaagtta aggaagcatg ttttggctta acggctggct    2880
taatgattgc ccaagatttt gtacgacttc atcctgatca aactgctatt gttatcggca    2940
gtgatattgc tcgctatggg gttaatactg ctggtgaagt tactcaagga gctggaagtg    3000
ttagtttatt aatttctagt aatccaagaa tttagaatt aaatgaaggc catagtgctt    3060
atagtgagga tatcaatgat ttctggcgcc ctaactattc taaaacagcc aaggtagatg    3120
gaaagtattc tacccaggtt tacttagact ttttcaaaca tactttttct gcttacaaag    3180
aacaaaagaa tcttgaaaca aaagattttg ccgctattgt ctaccactta ccttttacta    3240
agatgggatt aaaggcaaat agattagctg ttgagggaac ggatgaagaa acaaatgccc    3300
ggttaatgga cagctttact gcagctaaag aattgaatgc aaatgtaggt aatatttaca    3360
ctggatcgtt atacttgagt ctacttagtt tacttgaaaa tggtaggtta aaagctggag    3420
acttagtcgg tctatttcct tatggttcag gtgcaatggc tgaattttat tccgcaaatg    3480
tagttgaagg ctatgaaaaa caacttgata aggttggaga taaagcttta ttagataatc    3540
gaagcaagct tagtgttgcc gaatatgagg aaatcttttc tgcaggtttg gaagatccag    3600
aaaacaatgt tgaacttatc agtgatgaag aaactggtag atattatttt gctggtattc    3660
gtaatgatat ccgccaatat caagttaaat aacataagtc tctagtctcc ttagcaaata    3720
ttttagcata tgagacaagg caattagact taatgaaatt tataatatag gaaagataat    3780
tgtgaataaa aaaatagaag tcaaagcaca tggaaaagtg attcttattg gtgagcattc    3840
tgtagtttat ggctatgatg ccctcgctct tccaatccag gccttaaata tcaccacaac    3900
tgttgaagaa actgatggtc ctacttggat ggatacaact cattatcatg gtgctttttt    3960
tgatgcgccg gatgaatacg atggtattaa atatattgtg aaactttac ttgaaagagt    4020 agaaaacgct cctaatctta aaattactta tactggtgaa attcctatgg aacgggtttt    4080
tggatcaagt gctgttgtag ctttaggaac taccaaggct gtttcacaat tttaggatt     4140
```

```
aactctttct gaagctgaga tcatggaaat cactaatcat gcagaaatga ttaatcatgg    4200
aaaagcttcc ggccttgacg ctgctaccgt aaattccgat tacttagttt tcttcaataa    4260
acaagacgga ccaaaacagc tttctcaaaa attaggtgct accttattaa ttatggatac    4320
gggtgaactt ggaaatacca aagtcgcagt tcaatcagtt aaaaagcaaa tggatgaaag    4380
tgatcttaaa aagaaacaaa ttgcacggct tggagaatta gctaccgcaa cacgacaaaa    4440
ttggtttaac caaaatgcag aagagatcgg aagattttt aatgaagccg aagcatcct     4500 tgcctccttt aagctttcaa ctgaaagaat cgataatatt tgtaaaattg ccaatgaaaa    4560
tggcgcttta ggagctaaat tatctggtgg tggcttaggt ggcattgtaa ttgcactatg    4620
tcctaatcaa gaagttgcta aaaaaattgc cgaaaaagct aaagctaatt ttgataatga    4680
ctggattgag gaaattaat gaagaaaact gctcgtgccc acactaatat cgccttaatt    4740
aaatattggg gaaaagctga ccaagcttta aagacaccgt taatgtctag tctttcaatg    4800
acattagatg cctttatac tgatactaca tttgaacatg attcctcatt aactgaagat    4860
acctttattt taaatgatca aaaacaatca gtagaagaca gcaagcgagt ttttaattat    4920
attcatttat tacaagaaaa gtttggcgtt aatgaccact ttacaattcg gtctacaaac    4980
catgttccta cttctgctgg ccttgcttcc tcagcatcag cttttgcggc tcttgcaaca    5040
agctttgttg caagctatgg attagatctt tctaaaaagg agctttcaag acttgcacgc    5100
cttgggtctg ggtcagcgac tagatcagtt tatggcggct ttgttgaatg gaaaaagga    5160 tttgatgatg agagctccta tgcagctcca attgatgaaa atcctgatct tgatctttct    5220
ctactagcaa tcgaagttaa tacaaagcag aaaaaaattt cttcaacaaa aggaatgcag    5280
ttagcccaaa cctctccttt ttatcaacct tggttagcta gaaacgaaga gaaaattgct    5340
gaaattaaac aagctatcca aaataatgac tttactagaa ttggtgaact tagtgaacta    5400
agtgccaacg agatgcacgc ttgcaattta actgctaaag aaccctttac ttatttgaa    5460 ccggaaacaa ttaaaattat taaattagtt gaagatttaa gaaaaaatgg catcgaatgt    5520
tactatacaa ttgatgctgg tccaaacgta aaaattctct gcaccttaag aaatagaaaa    5580
gatattattt cagctgttca gaaaaccttg actaatgtta aatagtcgt tgcgagtttc    5640 ggcccaggcg ttactctgct ttagtaattt gaaaataaaa agattagagg aatattcgtt    5700
gattacagaa caagcaccag gaaagttgta tattgcggga gagtatgcag ttcttgagca    5760
aaactgccct gccattttag ttgcagtaaa tgaatttgta cgtgtttcaa ttgcaaagag    5820
tacaggtaca agtgggttaa ttcattctaa acagtattct caagattcaa ttcactggat    5880
ccgtaaaggt aaccaaatgg ttattgataa tcgtgataat ccgtttgaat acattttatc    5940
tgctattaac tttacagaac gttttgtct tgaacaaaaa gtttcaatgt ctttatatga    6000
cctacatgtt aattcagatc ttgattcagc cgacggtaaa aaatacggtc ttggctcttc    6060
agcggctgta acagttgcta cggtgaaggc tattcttaat ttctatggat tacactgtac    6120
aaaagatctt atttttaaac tttctgctat ttctcactat agcgttcaag gtaatggttc    6180
tgctggtgat attgcagcaa gtgtttacgg tggttggctt gcttatcaaa cttttgataa    6240
agcatggctt aagaaagaat tagctactaa atctcttagc gaagttttaa atgaagcttg    6300
gcctggtctt aagattcaat tattaactcc tccagaagga ctaaacttgg taattggttg    6360
gagtcaaaag cctgcttcaa cttctcaatt agttgataaa actaatgcaa agaaaaagtt    6420
tattaagact caatatgaca cttttttaga tgaatcacgg aaatgtgttc ttgatatgat    6480
```

```
taagggcttt aatgaaaaaa atatttcttt aattcaaaaa caaattcgtt taaatcgtca    6540
gttattaaaa gactttgctt ctcttaacca tattgctatc gaaatcccac gtttaactaa    6600
attaattaat attgccgaac aatttaatgg cgctgctaag acttctggtg caggaaatgg    6660
cgattgtggt attgtgattg cagatgaaaa aactgatatc gaagaaatga aaataattg     6720
gcgtaaaaat ggaattatgc cattgaactt tctagttcac tcaattgctt agtgggaaaa    6780
attatgtcac aaagatctca agaaaagaa gaacatctag cattagctaa gatgtttttt     6840
aatagtaata aagataatga ttttaatcat gttcatttaa tccgccctgc tcttccagaa    6900
agtgcaataa gtagagatag tatttcaact gaaatgtttg gtcatactat cagtactccc    6960
ttctttatta atgcaatgac tggcggctct gatacttcct ataccatcaa tcaacgttta    7020
gctaaagcgg ctgccgcaga aaatattccg atggctttag gatccgctag cattcttgaa    7080
aaagaaattg atcaaataga gagctttgaa gttgcacgtc aagaaaatcc tgatggacta    7140
atttttgcaa atgttaatcc aactactgat ccaaaagtag ctcaaaagat tgttgacgct    7200
ttagatgcaa atgcattaca gattcatctt aatagtgttc aagaagctgt aatgcctgaa    7260
ggcgatcgag attttcattg gatagataat ctaaaagaaa ttagagatac agttgatgtg    7320
ccaattatta ttaaagaagt tggaatggga attgatcctg aatctcttcg tacccttta     7380
atcaatgact tttcaattat cgatttaggt ggaagtggcg gaactaattt tgcgcaaatt    7440
gaaaatgaaa gacgaaagac tcaaaaatta aacttttag aagatattgg tctttctact     7500
gttaaaacgc tgcttgcagc acgcactatc cctgttaata aaactattat tgcagctggt    7560
ggcattacaa atgcactgga cattttaag tctttagttt taggtgcaca gtatgttggt     7620
attgcaaact atttcttgca gtatgctagc caagattccg agactttgat tgctgctatt    7680
caaaacttaa aatatgaatt gaacttttta actgctctat ttggtttaga tcatatttct    7740
aaagccgatg aagttagata ttatttggat actgatcttt acaatttcac tcgacaactc    7800
tataattagt tttaaaatat aagtgattta gatattcata atatatttgg gaggtaaatt    7860
aatatggaaa ccagaaggtc tgccaattat gaaccaaata gctgggatta tgattatttg    7920
ctgtcttctg acactgacga atctattgaa gtatacaaag acaaggccaa aaagctggag    7980
gctgaggtga aagagagat taacaatgaa aaggcagagt ttttgactct gcctgaactg    8040
atagataatg ttcaaaggtt aggattaggt tacagattcg agagtgacat aaggagagcc    8100
cttgatagat ttgtttcttc aggaggattt gatgctgtta caaaaactag ccttcatgct    8160
actgctctta gcttcaggct tctcagacag catggctttg aggtatctca agaagctttc    8220
agcggattca aggatcaaaa tggcaatttc ttgaaaaacc ttaaggagga catcaaggca    8280
atactaagcc tatatgaagc ttcatttctt gccttagaag gagaaaatat cttggatgag    8340
gccaaggtgt ttgcaatatc acatctaaaa gagcttagcg aagaaaagat tggaaaagac    8400
ctggccgaac aggtgaatca tgcattggag cttccattgc atagaaggac acaaagacta    8460
gaagctgttt ggagcattga agcatacaga aaaaaggaag atgcagatca agtactgcta    8520
gaacttgcta tattggacta caacatgatt caatcagtat accaaagaga tcttagagag    8580
acatcaaggt ggtggaggag agtgggtctt gcaacaaagt tgcattttgc tagagacagg    8640
ttaattgaaa gcttttactg gcagttgga gttgcatttg aacctcaata cagtgattgt     8700
agaaattccg tagcaaaaat gttttctttt gtaacaatca ttgatgatat ctatgatgtt    8760
tatggtactc tggatgagtt ggagctattt acagatgctg ttgagagatg ggatgttaat    8820
gccatcgatg atcttcctga ttatatgaag ctttgtttcc tagctcttta taacactatc    8880
```

```
aatgagatag cttatgataa tctgaaggac aagggggaaa acattcttcc atacctaaca    8940
aaagcatggg cagatttatg taatgcattc ctacaagaag caaaatggtt gtacaataag    9000
tccacaccaa catttgatga atatttcgga aatgcatgga aatcatcctc agggcctctt    9060
caactagttt ttgcctactt tgccgttgtt caaaacatca agaaagagga aattgataac    9120
ttacaaaagt atcatgatat catcagtagg ccttcccata tctttagact ttgtaacgac    9180
ttggcttcag catctgctga gatagcaaga ggtgaaaccg caaattctgt atcatgttac    9240
atgagaacaa aaggcatttc tgaggaactt gctactgaat ccgtaatgaa tttgatcgac    9300
gaaacctgga aaaagatgaa caaagaaaag cttggtggct ctctgtttgc aaaacctttt    9360
gttgaaacag ctattaacct tgcaagacaa tcccattgta cttatcataa cggagatgca    9420
catacttcac cagatgagct tactaggaaa agagtactgt cagtaatcac agagcctatt    9480
ctaccttttg agagataata atgctatttc gttggatggc tgctataagc agccatcctt    9540
tttgttttat ttatttttta aatgttaaag taacaatttt attaatttaa atataaaaag    9600
taaaaaagtt cattaaatta aatttggatc aataccaaaa gttaatttaa tgaacttcgt    9660
tctactaaat aacaaaagct aattaataat gttttagtc gacctgcagg catgcttggc     9720 actgccgtc gttttacaac gtcgtgactg ggaaaaccct ggcgttaccc aacttaatcg     9780
ccttgcagca catccccctt tcgccagctg gcgtaatagc gaagaggccc gcaccgatcg    9840
cccttcccaa cagttgcgca gcctgaatgg cgaatgcgc ctgatgcggt attttctcct     9900
tacgcatctg tgcggtattt cacaccgcat atggtgcact ctcagtacaa tctgctctga    9960
tgccgcatag ttaagccagc cccgacaccc gccaacaccc gctgacgcgc cctgacgggc    10020
ttgtctgctc ccggcatccg cttacagaca agctgtgacc gtctccggga gctgcatgtg    10080
tcagaggttt tcaccgtcat caccgaaacg cgcgagacga agggcctcg tgatacgcct     10140 atttttatag gttaatgtca tgataataat ggtttcttag acgtcaggtg gcacttttcg    10200
gggaaatgtg cgcggaaccc ctatttgttt attttttctaa atacattcaa atatgtatcc   10260
gctcatgaga caataaccct gataaatgct tcaataatat tgaaaaagga agagtatgag    10320
tattcaacat ttccgtgtcg cccttattcc cttttttgcg cattttgcc ttcctgtttt     10380 tgctcaccca gaaacgctgg tgaaagtaaa agatgctgaa gatcagttgg gtgcacgagt    10440
gggttacatc gaactggatc tcaacagcgg taagatcctt gagagttttc gccccgaaga    10500
acgttttcca atgatgagca cttttaaatt aaaaatgaag ttttaaaact tcattttaa     10560 tttaaattaa aaatgaagtt ttatcaaaaa aatttccaat aatcccactc taagccacaa    10620
acacgcccta taaatcccg ctttaatccc actttgagac acatgtaata ttactttacg     10680
ccctagtata gtgataattt tttacattca atgccacgca aaaaaataaa ggggcactat    10740
aataaaagtt ccttcggaac taactaaagt aaaaaattat ctttacaacc tccccaaaaa    10800
aaagaacagg tacaaagtac cctataatac aagcgtaaaa aatgagggt aaaaataaaa     10860 aaataaaaaa ataaaaaaat aaaaaaataa aaaaaataaa aaataaaaaa aataaaaaaa    10920
taaaaaaata aaaaaataaa aaaataaaaa aataaaaaaa tataaaaata aaaaaatata    10980
aaaataaaaa aatataaaaa taaaaaaata taaaaataaa aaaataaaaa aatataaaaa    11040
taaaaaaata aaaaaatata aaaatatttt ttatttaaag tttgaaaaaa atttttttat    11100
attatataat ctttgaagaa aagaatataa aaaatgagcc tttataaaag cccatttttt    11160
ttcatatacg taatatgacg ttctaatgtt tttattggta cttctaacat tagagtaatt    11220
```

```
tcttatttt  taaagcctt  ttcttaagg  gcttttattt  ttttcttaa  tacatttaat   11280
tcctcttttt  ttgttgcttt  tcctttagct  tttaattgct  cttgataatt  ttttttacct   11340
ctaatatttt  ctcttctctt  atattccttt  ttagaaatta  ttattgtcat  atattttgt    11400
tcttcttctg  taatttctaa  taactctata  agagtttcat  tcttatactt  atattgctta   11460
tttttatcta  aataacatct  ttcagcactt  ctagttgctc  ttataacttc  tctttcactt   11520
aaatgttgtc  taaacatact  attaagttct  aaaacatcat  ttaatgcctt  ctcaatgtct   11580
tctgtaaagc  tacaaagata  atatctatat  aaaaataata  taagctctct  gtgtccttt    11640
aaatcatatt  ctcttagttc  acaaagtttt  attatgtctt  gtattcttcc  ataaatataaa  11700
cttctttctc  tataaatata  atttattttg  cttggtctac  ccttttttcct  ttcatatggt   11760
tttaattcag  gtaaaaatcc  attttgtatt  tctcttaagt  cataaatata  ttcgtactca   11820
tctaatatat  tgactactgt  ttttgattta  gagtttatac  ttcctggaac  tcttaatatt   11880
ctggttgcat  ctaaggcttg  tctatctgct  ccaaagtatt  ttaattgatt  atataaaat   11940
tcttgaaccg  cttccataa   tggtaatgct  ttactaggta  ctgcatttat  tatccatatt   12000
aaatacattc  ctcttccact  atctattaca  tagtttggta  taggaatact  ttgattaaaa   12060
taattctttt  ctaagtccat  taatacctgg  tctttagttt  tgccagtttt  ataataatcc   12120
aagtctataa  acagtgtatt  taactctttt  atattttcta  atcgcctaca  cggcttataa   12180
aaggtattta  gagttatata  gatattttca  tcactctat   ctaaatcttt  taattcagcg   12240
tatttatagt  gccattggct  atatcctttt  ttatctataa  cgctcctggt  tatccaccct   12300
ttacttctac  tatgaatatt  atctatatag  ttcttttat   tcagctttaa  tgcgtttctc   12360
acttattcac  ctcccctct   gtaaaactaa  gaaaattata  tcatattttc  aataattatt   12420
aactattctt  aaactcttaa  taaaaaatag  agtaagtccc  caattgaaac  ttaatctatt   12480
ttttatgttt  taatttatta  tttttattaa  aatatttaa   actaaattaa  atgattcttt   12540
ttaattttt   actatttcat  tccataatat  attactataa  ttatttacaa  ataatatttc   12600
ttcatttgta  atatttagat  gatttactaa  ttttagtttt  tatatattaa  ataattaatg   12660
tataattat   ataaaaaatc  aaaggagctt  ataaattatg  attatttcca  aagatactaa   12720
agatttaatt  ttttcaattt  taacaatact  ttttgtaata  ttatgtttaa  atttaattgt   12780
atttttttca  tataataaag  ccgttgaagt  aaaccaatcc  attttcctta  tgatgttatt   12840
attaaattta  agttttataa  taatatcttt  attatattta  ttgtttttaa  aaaaactagt   12900
gaaatttccg  gctttattaa  acttattttt  aggaattta   ttttcattt   catctttaca   12960
ggatttgatt  atatctttaa  atatgtttta  tcaaatatta  tctttttcta  aatttatata   13020
tattttatt   atatttatta  ttatatatat  tttatttta   agtttcttc   taacagctat   13080
taaaagaaa   cttaaaaata  aaaacacgta  ctctaaacca  ataaataaaa  ctatttttat   13140
tattgctgcc  ttgattggaa  tagtttttag  taaaattaat  ttcaatattc  cacaatatta   13200
tattataagc  tagctttgca  ttgtacttt   caatcgcttc  acgaatgcgg  ttatctccga   13260
aagataaagt  cttttcatct  tccttgatga  agataagatt  ttctccgtct  ccgccggcag   13320
aattgaagcg  gggtactacg  gtatcgtctg  cgtcatcttc  cgttgtctga  tagatgatag   13380
tcataggctc  attttcttcc  gtttcggtaa  aggggatagg  ttcgcccttt  gagagcaggg   13440
cggcgatgga  aagcattaac  ttgctttttc  catcgcccgg  atctccctgc  aatagcgtaa   13500
ctttgccaaa  cggaatatac  ggataccaca  gccactttac  ttctttcggc  tcgatttcac   13560
ttgccttgat  gatttcaaga  ggtacgctga  aattcatttc  gttttcattt  agtttcattt   13620
```

```
tttcttgttc tccttttctc tgaaaatata aaaaccacag attgatacta aaaccttggt  13680
tgtgttgctt ttcggggctt aaatcaagga aaaatccttg ttttaagcct ttcaaaaaga  13740
aacacaaggt ctttgtacta acctgtggtt atgtataaaa ttgtagattt tagggtaaca  13800
aaaaacaccg tatttctacg atgttttttgc ttaaatactt gttttttagtt acagacaaac  13860 ctgaagttaa ctatttatca attcctgcaa ttcgtttaca aaacggcaaa tgtgaaatcc  13920
gtcacatact gcgtgatgaa cttgaattgc caaaggaagt ataattttgt tatcttcttt  13980
ataatatttc cccatagtaa aaataggaat caaataatca tatcctttct gcaaattcag  14040
attaaagcca tcgaaggttg accacggtat catagataca ttaaaaatgt tttccggagc  14100
atttggcttt ccttccattc tatgattgtt tccataccgt tgcgtatcac tttcataatc  14160
tgctaaaaat gatttaaagt cagacttaca ctcagtccaa aggctggaaa atgtttcagt  14220
atcattgtga atattgtat agcttggtat catctcatca tatatcccca attcaccatc  14280
ttgattgatt gccgtcctaa actctgaatg gcggtttaca atcattgcaa tataataaag  14340
cattgcagga tatagtttca ttccctttttc ctttatttgt gtgatatcca ctttaacggt  14400
catgctgtaa gtacaaggta cacttgcaaa gtagtggtca aaatactctt ttctgttcca  14460 actatttta tcaatttttt caaataccat ctaagttccc tctcaaattc aagtttatcg  14520
ctctaatgaa caaagatatt ataccacatt tttgtgaatt tttcaacttg cccacttcga  14580
ctgcactccc gacttaataa cttcttgaac acttgccgaa aagaaaaac tgccgggtac  14640 gtacccggga tcgatccccg ccgagcgctt agtgggaatt tgtacccctt atcgatacaa  14700
attccccgta ggcgctaggg acacttttc actcgttaaa aagttttgag aatattttat  14760 attttgttc atgtaatcac tccttcttaa ttacaaattt ttagcatcta atttaacttc  14820
aattcctatt atacaaaatt ttaagatact gcactatcaa cacactctta agtttgcttc  14880
taagtcttat ttccataact tcttttacgt ttccgggtac aattcgtaat catgtcatag  14940
ctgtttcctg tgtgaaattc ttatccgctc acaattccac acaacatacg agccggaagc  15000
ataaagtgta aagcctgggg tgcctaatga gtgagctaac tcacattaat tgcgttgcgc  15060
tcactgcccg ctttccagtc gggaaacctg tcgtgccaga aaacttcatt tttaatttaa  15120
aaggatctag gtgaagatcc ttttttgataa tctcatgacc aaaatccctt aacgtgagtt  15180
ttcgttccac tgagcgtcag accccgtaga aagatcaaa ggatcttctt gagatccttt  15240
ttttctgcgc gtaatctgct gcttgcaaac aaaaaaacca ccgctaccag cggtggtttg  15300
tttgccggat caagagctac caactctttt tccgaaggta actggcttca gcagagcgca  15360
gataccaaat actgtccttc tagtgtagcc gtagttaggc caccacttca agaactctgt  15420
agcaccgcct acatacctcg ctctgctaat cctgttacca gtggctgctg ccagtggcga  15480
taagtcgtgt cttaccgggt tggactcaag acgatagtta ccggataagg cgcagcggtc  15540
gggctgaacg gggggttcgt gcacacagcc cagcttggag cgaacgacct acaccgaact  15600
gagataccta cagcgtgagc tatgagaaag cgccacgctt cccgaaggga gaaaggcgga  15660
caggtatccg gtaagcggca gggtcggaac aggagagcgc acgagggagc ttccaggggg  15720
aaacgcctgg tatctttata gtcctgtcgg gtttcgccac ctctgacttg agcgtcgatt  15780
tttgtgatgc tcgtcagggg ggcggagcct atggaaaaac gccagcaacg cggccttttt  15840
acggttcctg gccttttgct ggccttttgc tcacatgttc tttcctgcgt tatcccctga  15900
ttctgtggat aaccgtatta ccgcctttga gtgagctgat accgctcgcc gcagccgaac  15960
```

```
gaccgagcgc agcgagtcag tgagcgagga agcggaagag cgcccaatac gcaaaccgcc   16020
tctccccgcg cgttggccga ttcattaatg cagctggcac gacaggtttc ccgactggaa   16080
agcgggcagt gagcgcaacg caattaatgt gagttagctc actcattagg caccccaggc   16140
tttacacttt atgcttccgg ctcgtatgtt gtgtggaatt gtgagcggat aacaatttca   16200
cacaggaaac agctatgacc atgattac                                       16228
```